(12) United States Patent
Yang et al.

(10) Patent No.: US 7,166,451 B1
(45) Date of Patent: Jan. 23, 2007

(54) IMMOBILIZATION OF ENZYME ON A FIBROUS MATRIX

(75) Inventors: Shang-Tian Yang, Dublin, OH (US); Nedim Albayrak, Van (TR)

(73) Assignee: The Ohio State University, Columbus, OH (US)

( * ) Notice: Subject to any disclaimer, the term of this patent is extended or adjusted under 35 U.S.C. 154(b) by 425 days.

(21) Appl. No.: 10/785,274

(22) Filed: Feb. 24, 2004

Related U.S. Application Data

(60) Provisional application No. 60/449,691, filed on Feb. 24, 2003.

(51) Int. Cl.
*C12N 11/06* (2006.01)
*C12N 11/08* (2006.01)

(52) U.S. Cl. ..................... 435/182; 435/180
(58) Field of Classification Search ............... 435/180, 435/182
See application file for complete search history.

(56) References Cited

U.S. PATENT DOCUMENTS

| | | | | |
|---|---|---|---|---|
| 4,251,631 | A * | 2/1981 | Simon ..................... | 435/106 |
| 4,572,897 | A * | 2/1986 | Amotz et al. ............ | 435/177 |
| RE33,441 | E * | 11/1990 | Wumpelmann et al. .... | 435/180 |
| 5,057,421 | A * | 10/1991 | Hofmann et al. ......... | 435/182 |
| 5,412,087 | A * | 5/1995 | McGall et al. ........... | 436/24.3 |
| 5,472,861 | A * | 12/1995 | Lantero et al. ........... | 435/188 |
| 5,541,097 | A * | 7/1996 | Lantero et al. ........... | 435/188 |
| 5,563,056 | A * | 10/1996 | Swan et al. .............. | 435/180 |
| 5,759,578 | A * | 6/1998 | Soon-Shiong et al. .... | 424/484 |
| 5,939,294 | A * | 8/1999 | Sarkki et al. ............. | 435/100 |

OTHER PUBLICATIONS

Talabardon et al., "Acetic Acid Production from Lactose by an Anaerobic Thermophilic Coculture Immobilized in a Fibrous-Bed Bioreactor", Biotechnol. Prog. 2000, 16, pp. 1008-1017.
Huang et al., "Acetate Production from Whey Lactose Using Co-Immobilized Cells of Homolactic and Homoacetic Bacteria in a Fibrous-Bed Bioreactor", Biotechnology and Bioengineering, vol. 60, No. 4, Nov. 20, 1998, pp. 498-507.
Yang et al., "Production of Cell-Free Xanthan Fermentation Broth by Cell Adsorption on Fibers", Biotechnol. Prog. 1998, 14, pp. 259-264.
Yang et al., "A Novel Recycle Batch Immobilized Cell Bioreactor for Propionate Production from Whey Lactose", Biotechnology and Bioengineering, vol. 45, (1995), pp. 379-386.
Albayrak et al., "Production of Galacto-Oligosaccharides From Lactose by *Aspergillus oryzae* β -Galactosidase Immobilized on Cotton Cloth", Biotechnology and Bioengineering, vol. 77, No. 1, Jan. 5, 2002, pp. 8-19.
Zemek et al., "Crosslinked polyethylenimine: and enzyme carrier with spacers of various lengths introduced in crosslinking reaction", Enzyme Microb. Technol., 1982, vol. 4, Jul., pp. 233-238.
Jendrisak et al., "The Use of Polyethyleneimine in Protein Purification", Protein Purification: Micro to Macro, Proceedings of a Cetus-UCLA Symposium Held at Frisco, Colorado, Mar. 29-Apr. 4, 1987, pp. 75-97.
Wasserman et al., "High-Yield Method for Immobilization of Enzymes", Biotechnology and Bioengineering, vol. XXII, (1980), pp. 271-287.
Emneus et al., "Comparison between different inorganic supports for the immobilization of amyloglucosidase and α -amylase to be used in enzyme reactors in flow-injection systems," Analytica Chimica Acta, 276 (1993), pp. 319-328.
Yang et al., "A Dynamic Light Scattering Study of β -Galactosidase: Environmental Effects on Protein Conformation and Enzyme Activity", Biotechnol. Prog. 1994, 10, pp. 525-531.
Kumar et al., "Whole blood glucose determination using glucose oxidase immobilized on cotton cheese cloth", Analytica Chimica Acta 338 (1997), pp. 135-140.
Kamath et al., "Urease Immobilized on Polyethyleneimine Cotton Cloth", Applied Biochemistry and Biotechnology, vol. 19, 1988, pp. 251-258.
Das et al., "Short Communication: Immobilization of urease from pigeonpea (*Cajanus cajan* L.) on flannel cloth using polyethyleneimine", World Journal of Microbiology & Biotechnology, vol. 14, 1998, pp. 927-929.
Uamazaki et al., "Immobilization of Invertase on Polyethylenimine-Coated Cotton Cloth", Biotechnology Letters, vol. 6, No. 3, (1984), pp. 165-170.
D'Souza et al., "Cloth Bioreactor containing yeast cells immobilized on cotton cloth using polyethylenimine", Appl Microbiol Biotechnol (1988), 29, pp. 136-140.
Sako et al., "Recent progress on research and applications of non-digestible galacto-oligosaccharides", International Dairy Journal 9 (1999), pp. 69-80.
Playne et al., "1. Commercially Available Oligosaccharides", Bulletin of the IDF 313, pp. 10-22, 1996.
Shin et al., "Continuous production of galacto-oligosaccharides from lactose by *Bullera singularis* β -galactosidase immobilized in chitosan beads", Process Biochemistry, vol. 33, No. 8, 1998, pp. 787-792.

(Continued)

*Primary Examiner*—Herbert J. Lilling
(74) *Attorney, Agent, or Firm*—Dinsmore & Shohl LLP

(57) ABSTRACT

A multilayer enzyme immobilization process is provided comprising adsorbing a polyethyleneimine (PEI) solution in a fibrous matrix, and adding an enzyme to the fibrous matrix, which comprises a plurality of fibrils. The process further comprises forming at least two layers of PEI-enzyme aggregates on the fibrils, and cross-linking the multilayer PEI-enzyme aggregates. The process can further comprise washing the fibrils containing the cross-linked PEI-enzyme aggregates with distilled water and acetic acid buffer subsequent to cross-linking. However, the PEI-containing matrix is not washed prior to the addition of enzyme. The enzyme can be β-galactosidase and the fibrous matrix can be cotton cloth. The multilayer immobilized enzyme can be employed in a biocatalyst reactor for production of galacto-oligosaccharides from lactose and the hydrolysis of lactose to glucose and galactose.

36 Claims, 9 Drawing Sheets

OTHER PUBLICATIONS

Foda et al., "Continuous production of oligosaccharides from whey using a membrane reactor", Process Biochemistry 35 (2000), pp. 581-587.

Yang et al., "Novel Products and New Technologies for Use of a Familiar Carbohydrate, Milk Lactose", Journal of Dairy Science, vol. 78, No. 11, 1995, pp. 2541-2562.

Berger et al., "Oligosaccharides Synthesis by Free and Immobilized α-Galactosidases From *Thermus aquaticus* YT-1", Biotechnology Letters, vol. 17, No. 10. (Oct. 1995), pp. 1077-1080.

Mozaffar et al., "Effect of glutaraldehyde on oligosaccharide production by β -galactosidase from *Bacillus circulans*", Appl Microbiol Biotechnol (1987) 25, pp. 426-429.

Matsumoto et al., "Production of Galactooligosaccharides with β-Galactosidase", Denpun Kagaku, vol. 36, No. 2, (1989), pp. 123-130.

Mozaffar et al., "Continuous production of galacto-oligosaccharides from lactose using immobilized β -galactosidase from *Bacillus circulans*", Appl Microbiol Biotechnol (1986) 25, pp. 224-228.

Sheu et al., "Production of galactooligosaccharides by β-galactosidase immobilized on glutaraldehyde-treated chitosan beads", Biotechnology Techniques, vol. 12, No. 4, Apr. 1998, pp. 273-276.

Kminkova et al., "Immobilization of Mold Beat-Galactosidase", Collection Czechoslovak Chem. Commun. (vol. 53), (1988), pp. 3214-3219.

Berger et al., "Immobilization of β-Galactosidases From *Thermus aquaticus* YT-1 for Oligosaacharides Synthesis", Biotechnology Techniques, vol. 9, No. 8, (Aug. 1995), pp. 601-606.

Prenosil et al., "Formation of Oligosaccharides during Enzymatic Lactose: Part I: State of Art", Biotechnology and Bioengineering, vol. 30, (1987), pp. 10-19-1025.

Pedersen et al., "Enzyme Adsorption in Porous Supports: Local Thermodynamic Equilibrium Model", Biotechnology and Bioengineering, vol. XXVII, (1985), pp. 961-971.

Dissing et al., "Polyelectrolyte complexes as vehicles for affinity precipitation of proteins", Journal of Biotechnology, 52, (1996), pp. 1-10.

Prenosil et al., "Formation of Oligosaccharides during Enzymatic Lactose Hydrolysis and Their Importance in a Whey Hydrolysis Process: Part II: Experimental", Biotechnology and Bioengineering, vol. 30, (1987), pp. 1026-1031.

Rugh, "A Comparison of the Formation of Intermediary Products During Lactose Hydrolysis with Free and Immobilized Thermophilic Lactase", Applied Biochemistry and Biotechnology 7 (1982), pp. 27-29.

Prenosil et al., "Scale-Up of Membrane Fixed Enzyme Reactors: Modelling and Experiments", Desalination, 53 (1985), pp. 265-278.

Boon et al., "Effect of temperature and enzyme origin on the enzymatic synthesis of oligosaccharides", Enzyme and Microbial Technology 26 (2000), pp. 271-281.

Onda et al., "Activity and Stability of Glucose Oxidase in Molecular Films Assembled Alternately with Polyions", Journal of Bioscience and Bioengineering, vol. 87, No. 1, 1999, pp. 69-75.

Dekker, "Immobilization of a Lactase onto a Magnetic Support by Covalent Attachment to Polyethyleneimine-Glutaraldehyde-Activated Magnetite", Applied Biochemistry and Biotechnology, vol. 22, 1989, pp. 289-310.

Bardeletti, "Enzyme Immobilization om Polyethyleneimine-Coated Magnetite Particles", Methods in Biotechnology, vol. 1: Immobilization of Enzymes and Cells, Edited by G.F. Bickerstaff Humana Press Inc., Totowa, NJ, 1997, pp. 133-141.

Mateo et al., "Reversible Enzyme Immobilization via a Very Strong and Nondistorting Ionic Adsorption on Support- Polyethylenimine Composites", Biotechnology and Bioengineering, vol. 68, No. 1, Apr. 5, 2000, pp. 98-105.

Isgrove et al., "Enzyme immobilization on nylon-optimization and the steps used to prevent enzyme leakage from the support", Enzyme and Microbial Technology 28 (2001), pp. 225-232.

Iwasaki et al. "Galacto-oligosaccharide Production from Lactose by an Enzymic Batch Reaction Using β -Galactosidase", Process Biochemistry, vol. 31, No. 1, 1996, pp. 69-76.

Monsan et al., "Enzymatic synthesis of oligosaccharides", FEMS Microbiology Reviews 16, (1995), pp. 187-192.

Yang et al., "Production of Galacto-Oligosaccharides from Lactose by Immobilized β -Galactosidase" In Applied Biocatalysis in Specialty Chemicals and Pharmaceuticals, ACS Symposium 776, American Cancer Society, Washington, DC, Chapter 9, pp. 131-154, (2000).

Bryjak, "Storage stabilization of enzyme activity by poly(ethyleneimine)", Bioprocess Engineering 13, (1995), pp. 177-181.

Noworyta, "Kinetic behaviour of penicillin acylase stabilized by poly(ethyleneimine)", Bioprocess Engineering 13, (1995), pp. 183-187.

Margolin et al., "Preparation and Properties of Penicillin Amidase Immobilized in Polyelectrolyte", Biochemica et Biophysica Acta, 660 (1981), pp. 359-365.

Margoliln et al., "Enzymes in polyelectrolyte complexes" The effect of phase transition on thermal stability, Eur. J. Biochem. 146, (1985), pp. 625-632.

Fernandez-Lafuente et al., "Stabilization of immobilized enzymes against organic solvents: complete hydrophylization of enzymes environments by solid-phase chemistry with poly-functional macromolecules", Prog. Biotechnol., 15, 1998, pp. 405-410.

Fernandez-Lafuente et al., "Immobilization of lipases by selective adsorption on hydrophobic supports", Chem. Phys. Lipids, 93, 1998, pp. 185-187.

Khan et al., "Surfactant hydrophobic effect on the phase behavior of oppositely charged protein and surfactant mixtures: Lysozyme and sodium alkyl sulfates" Langmuir, 14, 1998, pp. 6818-6826.

Suominen et al., "Enhanced recovery and purification of *Aspergullus* glucoamylase from *Saccharomyes cerevisiae* by the addition of poly(aspartic acid) tails", Enzyme Microb. Technol., 15, 1998, pp. 593-600.

Parker et al., "Recovery of a Charged-Fusion Protein from Cell Extracts by Polyelectrolyte Precipation", Biotechnology and Bioengineering, vol. 36, (1990), pp. 467-475.

Zhao et al., Polyelectrolyte precipitation of β-galactosidase fusions containing poly-aspartic acid tails, Journal of Biotechnology , 14 (1990), pp. 273-284.

Caruso et al., "Enzyme Multilayers and Colloid Particles: Assembly, Stability, and Enzymatic Activity", Langmuir 2000, 16, pp. 9595-9603.

Bahulekar et al., "Polyethyleneimine in immobilization of biocatalysts", Enzyme Microb. Technol., 1991, vol. 13, Nov., pp. 858-868.

Kawai et al., "High Conversion in Asymmetric Hydrolysis during Permeation through Enzyme-Multilayered Porous Hollow-Fiber Membranes", Biotechnol. Prog. 2001. 17. pp. 872-875.

Axelsson et al., "Economic Evaluation of the Kydrolysis of Lactose Using Immobilized β -Galactosidase", Applied Biochemistry and Biotechnology, vol. 24/25, 1990, pp. 679-693.

Howlett et al., "Carbonyldimidazole Activation of a Rayon/Polyester Cloth for Covalent Immobilization of Proteins", Biotechnology Techniques, vol. 5, No. 5, 1991, pp. 395-400.

Mozaffar et al., "Purification and Properties of β-Galactosidases from *Bacillus circulans*", Agric. Biol. Chem, 48 (12), 1984, pp. 3053-3061.

* cited by examiner

IMMOBILIZATION OF ENZYME ON A FIBROUS MATRIX

CROSS-REFERENCE TO RELATED APPLICATION

This application claims the benefit of U.S. Provisional Application Ser. No. 60/449,691, filed Feb. 24, 2003 and entitled "IMMOBILIZATION OF β-GALACTOSIDASE ON A FIBROUS MATRIX", the disclosure of which is incorporated herein by reference.

STATEMENT REGARDING FEDERALLY SPONSORED RESEARCH OR DEVELOPMENT

This invention was made with government support under USDA/CSREES Agreement No. 98-35503-6325 and USDA-SBIR Proposal No. 2001-00279, awarded by the United States Department of Agriculture. The U.S. government has certain rights in this invention.

BACKGROUND OF THE INVENTION

The present invention relates to enzyme immobilization on fibrous matrices and, more particularly, to immobilization of β-galactosidase on a fibrous matrix for production of galacto-oligosaccharides from lactose.

Biocatalyst immobilization is gaining increased attention for the synthesis of industrial bioproducts ranging from neutraceuticals to chemicals. Enzyme immobilization provides many important advantages over use of enzymes in soluble form, namely, enzyme reusability, continuous operation, controlled product formation, and simplified and efficient processing. The main challenges in enzyme immobilization include not only containment of a large amount of enzyme to be immobilized while retaining most of its initial activity, but also the performance of immobilized enzyme in actual production processes in industrial-type reactors. Thus, the success of immobilized enzyme is not only driven by its applications but also relies on a number of factors, including enzyme support, chemical reagent, and reactor.

Enzyme support is generally considered as the most important component contributing to the performance of the immobilized biocatalyst reactor. In addition to being a very inexpensive and widely available fibrous material, cotton cloth provides a number of desirable characteristics, including high porosity (>95%), large specific surface area, and excellent mechanical strength. Cotton cloth has been successfully used in cell immobilization and fermentation studies. Cotton cloth immobilized enzyme placed in a loose spiral shape in a plug-flow-type reactor provides good flow rates, low pressure drop, and negligible mass transfer resistance. These characteristics are also highly desirable for industrial enzyme application. Thus, cotton fabric also can be used for the development of an industrially applicable fibrous bed enzyme bioreactor where the immobilized enzyme functions as good as soluble enzyme.

Although enzymes can be immobilized on cotton cloth activated with tosyl chloride, the method is somewhat tedious and involves the use of organic chemicals. Polyethyleneimine (PEI), an extremely branched cationic chain polymer, has many applications in biochemistry because of its electrostatic interaction with negatively charged species. PEI has been an essential ingredient of many enzyme immobilization procedures, where it serves to coat an inert support such as porous glass microbeads or charged insoluble carriers. Cotton cloth coated with PEI has been used as a support for immobilization of several enzymes, including glucose oxidase, urease, and invertase, and yeast cells. In these applications, PEI is adsorbed on the cotton cloth and then excess PEI is washed away with water or buffer solution. The remaining PEI is then cross-linked with glutaraldehyde before and/or after enzyme coupling. However, the amount of enzyme immobilized is rather low and needs to be improved for industrial applications.

Lactose found in cheese whey is an abundant byproduct from the dairy industry and can be used to produce galacto-oligosaccharides (GOS), a prebiotic functional food ingredient that selectively stimulates the growth of bifidobacteria in the lower part of the human intestine. Commercial potential for applications of galacto-oligosaccharides in food product lines is high because of its many health benefits, but an economical production process still needs to be developed. There has been a steady 3% annual increase in cheese production. The already problematic lactose is thus expected to be a major concern for the dairy industry. Although there has been extensive research for better utilization of whey lactose, the dairy industry is still in need of new technologies for converting lactose into marketable products. Thus, converting lactose into a valuable food ingredient such as galacto-oligosaccharides that is free of problems associated with lactose is of benefit and highly desirable by the food industry.

Production of galacto-oligosaccharides by immobilized β-galactosidase has been considered in several studies. However, galacto-oligosaccharide production from immobilized enzymes has not been addressed very well. Many of the carriers used for immobilization of β-galactosidases applied in galacto-oligosaccharide production are types of microparticles, such as ion exchange resins, chitosan beads, cellulose beads, and agarose beads. In addition to operational (back pressure, aggregation, clogging) and economical (expensive) disadvantages, commonly noted diffusion limitations in these immobilized systems not only reduce the reaction rate in general but also affect the product spectrum and specifically reduce galacto-oligosaccharide formation. For example, 20–30% decreases in the galacto-oligosaccharide formation have been reported with immobilized enzymes due to introduction of mass transfer resistance in the system.

Accordingly, there is a recognized need for improvements in methods of enzyme immobilization on fibrous matrices design.

SUMMARY OF THE INVENTION

The present invention meets the above-mentioned need by providing a multilayer enzyme immobilization process on fibrous matrices involving polyethyleneimine (PEI). Although the present invention is not limited to specific advantages or functionality, it is noted that compared to the large body of enzyme immobilization systems available, multilayer enzyme immobilization on cotton cloth can be considered as one of the cheapest, safest, fastest, and most successful of such systems. Fibrous support offers great advantages over particulate resins or porous beads in industrial scale enzyme immobilization. The process is simple and straightforward and requires no sophisticated expertise, which is unlike many other enzyme immobilization methods. There is no need for prior activation of carriers or using any special apparatus, which is a great burden for large- and small-scale industrial applications.

The U.S. Food and Drug Administration has approved PEI for use in the production of food ingredients. The multilayered PEI process of the present invention provides high enzyme loading up to about 500 mg/g fibrous matrix, e.g., cotton cloth, and up to about 100% enzyme immobilization yield. Typically, the process provides for enzyme loading that is between about 150 and about 250 mg/g fibrous matrix, and at least about 5% enzyme immobilization yield. However, enzyme loading and yield values can fluctuate depending upon the particular PEI and enzyme that is employed. The high enzyme loading results in exceptionally high reactor productivity yet does not affect the product, e.g., galacto-oligosaccharide, formation kinetics as compared with soluble enzyme. This immobilized enzyme technology therefore provides for important application in galacto-oligosaccharide production from lactose and can be applied to other enzymes as well, such as, for example, lipase, lactate dehydrogenase, formate dehydrogenase, glucose isomerase, etc.

In accordance with one embodiment of the present invention, a multilayer enzyme immobilization process is provided. The process comprises adsorbing a PEI solution in a fibrous matrix, the matrix including a plurality of fibrils; adding an enzyme in solution to the fibrous matrix containing the PEI solution; forming at least two layers of PEI-enzyme aggregates on the fibrils; and cross-linking the multilayered PEI-enzyme aggregates with an enzyme fixative, for example, glutaraldehyde. The process can further comprise washing the fibrils containing the cross-linked PEI-enzyme aggregates with distilled water and acetic acid buffer subsequent to cross-linking. The enzyme can be β-galactosidase from *A. oryzae, B. circulans, K. lactis*, or combinations thereof, and the fibrous matrix can be cotton cloth, poly(ethylene terephthalate), or rayon, inter alia. The immobilized enzyme produced by the process of the present invention can be applied in the production of galacto-oligosaccharides from lactose and hydrolysis of lactose to glucose and galactose. Also contemplated is the use of the process of the present invention in other bioprocessing applications, such as, for example, the esterification of organic acids with alcohols to form esters with lipase immobilized on a fibrous matrix, and co-immobilization of lactate dehydrogenase and formate dehydrogenase to a NADH dependent coupled enzyme reaction to produce drug intermediates.

In accordance with another embodiment of the present invention, a fibrous-bed biocatalyst reactor is provided comprising a fibrous matrix and a vessel, such as, for example, a glass column. The fibrous maxtrix comprises multilayer immobilized PEI-enzyme aggregates produced by the enzyme immobilization process described herein, and a steady flow of lactose solution can be fed through the vessel (reactor) for production of galacto-oligosaccharides. Accordingly, a method of producing galacto-oligosaccharides from lactose using immobilized multilayer PEI-enzyme aggregates is also described.

These and other features and advantages of the invention will be more fully understood from the following detailed description of the invention taken together with the accompanying drawings.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
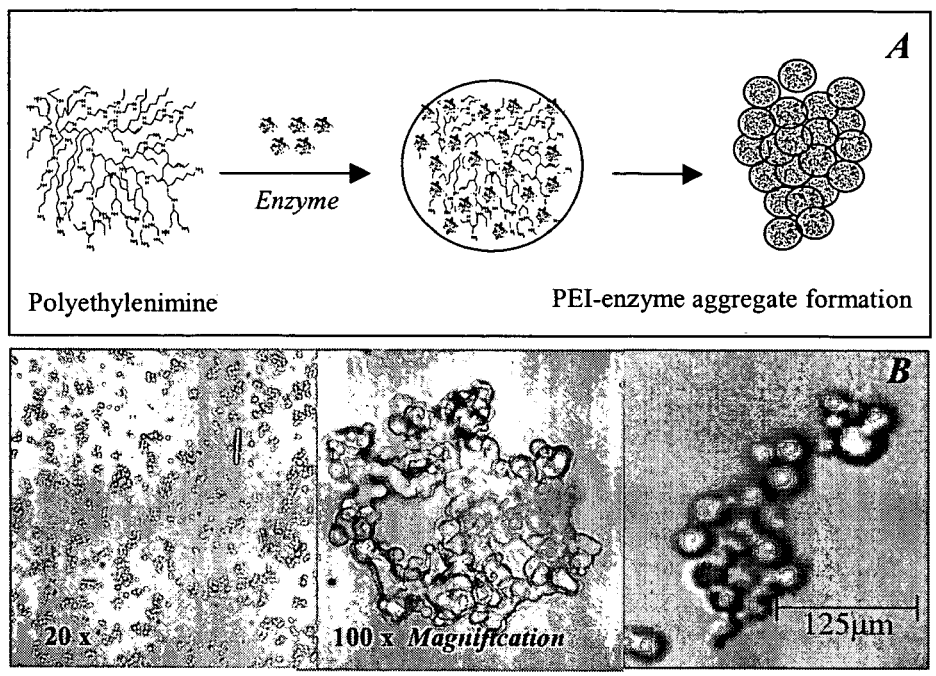
FIG. 1 is a schematic illustration of the proposed mechanism for PEI-enzyme aggregate formation (A) and a photograph of the morphology of PEI-enzyme aggregates in solution seen under a light microscope (B)

Skilled artisans appreciate that elements in the figures are illustrated for simplicity and clarity and have not necessarily been drawn to scale. For example, the dimensions of some of the elements in the figures may be exaggerated relative to other elements to help improve understanding of embodiment(s) of the present invention.

DETAILED DESCRIPTION OF PREFERRED EMBODIMENTS OF THE INVENTION

In accordance with one embodiment of the present invention, a multilayer enzyme immobilization process is provided comprising adsorbing a solution of PEI dissolved in water in the fibrous matrix, and adding the enzyme to the fibrous matrix that contains the PEI solution. The concentration of PEI in solution can be between about 0.001 mg/mL and the solubility of PEI in water. Typically, the concentration of PEI in water is about 2 mg/mL. The fibrous matrix can comprise any material forming fibers and typically comprises cotton cloth in a knitted form (i.e., cotton terry cloth), as well as various other types of fibrous materials with different physical (e.g., knitted, non-woven) and chemical characteristics, including, for example, poly(ethylene terephthalate) (PET), glass fiber, wool, carbon fiber, ceramic fiber, paper, rayon (restructured cellulose), and combinations thereof, each comprising a plurality of fibrils. By "fibrils" we mean individual fiber filament. In the case of natural cotton fiber, the filament fibrils typically present as a bundle.

The enzyme can comprise a galactosidase, such as β-galactosidase, an enzyme that hydrolyzes the beta galactoside linkage in lactose to produce glucose and galactose. Other functional enzymes can be immobilized as well in accordance with the present invention, such as, for example, lipase, lactate dehydrogenase, formate dehydrogenase, glucose isomerase, etc. The β-galactosidase employed in accordance with the present invention can be isolated from a microorganism such as *A. oryzae, A. niger, B. circulans, B. singularis, T. aquaticus, K. lactis,* or *E. coli.* Typically, the enzyme is β-galactosidase obtained from *A. oryzae, B. circulans,* or *K. lactis.* The process further comprises forming PEI-enzyme aggregates on the fibrils, and cross-linking the formed PEI-enzyme aggregates with an enzyme fixative, including, for example, gluteraldehyde, formaldehyde, or any aldehydes or keto compound that can form covalent bonds with the amine groups of the enzyme protein. In addition, the process can further comprise washing the fibrils and the cross-linked PEI-enzyme aggregates formed thereon with distilled water and acidic buffer subsequent to cross-linking.

PEI-Enzyme Aggregate Formation. While not wishing to be bound by any particular theory, it is contemplated that PEI-enzyme association and precipitation are the driving force of enzyme immobilization on a fibrous matrix, such as cotton cloth. Therefore, the formation of PEI-enzyme aggregates in solution is described herein. When a clear enzyme solution in distilled water is mixed with a PEI solution, a cloudy, turbid, or "milky" slurry of PEI-enzyme aggregates is formed instantaneously. It is well-known that although the highly branched and positively charged PEI molecules form electrostatic complexes with negatively charged species such as proteins and nucleic acids, still larger particles (i.e., PEI-enzyme aggregates) are observed in the initial homogeneous milky solution, which particles eventually precipitate upon standing. A proposed mechanism for the PEI-enzyme association leading to the formation of aggregates is shown in FIG. 1A, which also reflects the relative sizes of PEI (MW 750,000) and enzyme (MW 110,000) used in the example. It should be understood, however, that in accordance with the present invention, PEI with different molecular weights, both smaller and larger, can be used for the aggregation. FIG. 1B shows the morphology of PEI-enzyme aggregates observed under a light microscope, which aggregates are approximately 10–50 μm in diameter.

Figure 4:
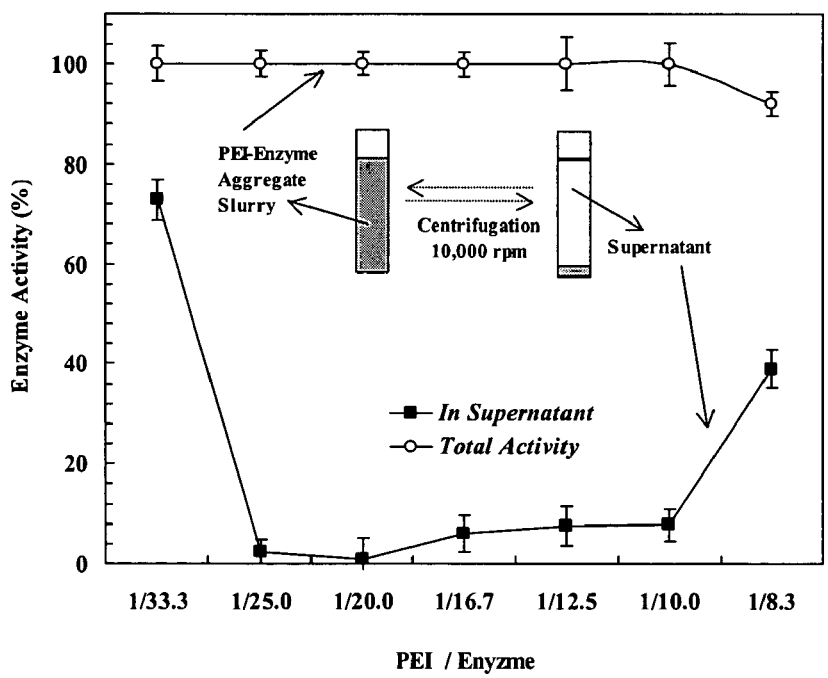
FIG. 4 is a graphical illustration of the effect of PEI to enzyme ratio on enzyme activities of PEI-enzyme aggregates in solution and in supernatant after centrifugation at 10,000 rpm for 1 min.

The effect that various factors, such as PEI to enzyme ratio, pH, and presence of buffer, have on the activity of PEI-enzyme aggregates (and remaining activity in the supernatant after centrifugation of the cloudy solution) are also described. As shown in FIG. 4, if the initial pH of the PEI solution is adjusted to ~8.0, the concentration of PEI does not affect enzyme activity at the ratios of PEI to enzyme shown (i.e., from 1/33.3 to 1/8.3). Here, for example, the amount of PEI used was increased by a factor of 4 and the enzyme amount was fixed. Also, PEI-enzyme aggregate formation (cloudy solution) does not necessarily yield precipitation. In accordance with the present invention, a PEI to enzyme ratio of between about 1/33.3 and about 1/8.3 is preferred. However, literally any ratio will yield some enzyme immobilization. PEI can be any amount from about 0.001 to about 30 mg/mL and enzyme can be any amount from about 0.001 to 100 mg/mL. What is important is that there is a balanced charge ratio between PEI (positive charge) and enzyme (negative charge). This ratio can vary depending upon the different PEI or enzyme used and will need to be adjusted according to the charge density under the solution condition. For β-galactosidase, the highest amount of enzyme precipitate is typically obtained at the PEI to enzyme weight (mg/mg) ratio of between about 1/20 and about 1/25, while higher or lower ratios yielded ineffective particle formation that stayed in solution. A PEI to enzyme ratio of 1/50 will produce a lightly turbid solution but no precipitation even after centrifugation, while a ratio of 1/100 will produce no turbidity and no precipitation at all.

In addition to PEI to enzyme ratio, pH and presence of negatively charged salt ions in the buffer solution were also found to be factors affecting PEI-enzyme aggregate formation and the final activity of the complex. PEI-enzyme aggregate formation can occur at a pH between about 4 and about 10. However, a pH range of between about 6 and about 8 is preferred, where similar precipitation and activity can be obtained. If the pH of PEI-enzyme slurry is lowered to below 5, especially below 4, the turbid solution will become clear and no precipitation will occur. Also, at pH values above 8, although aggregation and precipitation are not affected, the enzyme will likely lose its activity. When the enzyme solution is prepared in acetate or phosphate buffer (0.1 M), regardless of the pH, most of the enzyme, ca. 90–95%, will stay in the solution. Thus, PEI-enzyme aggregate formation is totally reversible. The aggregates can be dissociated upon lowering the pH, and the enzyme in the PEI-enzyme complex can be replaced by small negatively charged species.

Enzyme Immobilization on Cotton Cloth—Multilayer Immobilization. In light of the foregoing with respect to PEI-enzyme aggregate formation in solution, in accordance with the present invention, the multilayer enzyme immobilization process comprises adsorbing a PEI solution in a fibrous matrix, which matrix includes a plurality of fibrils; adding an enzyme in solution to the fibrous matrix that contains the PEI solution; forming at least two layers of PEI-enzyme aggregates on the fibrils; and cross-linking the PEI-enzyme aggregates. As noted herein, the fibrous matrix is typically cotton cloth. The enzyme can be β-galactosidase obtained from *A. oryzae, B. circulans,* or *K. lactis.* However, other enzymes can be immobilized in accordance with the present invention.

Bahulekar et al. describe a process wherein PEI is first adsorbed on cotton cloth and then the excess PEI is washed away with water or buffer solution, resulting in a low efficiency for enzyme immobilization (see Bahulekar et al. Polyethyleneimine in immobilization of biocatalysts.

*Enzyme Microb. Technol.* 1991, 13, 858–868). It is important to note that cotton cloth lacks any specific adsorption capacity for PEI except a rough surface and high porosity. Although not wishing to be bound by any particular theory, it is contemplated that since positively charged PEI molecules would strongly repel one another, only a "monolayer" of PEI is expected to form on the fibrils of cotton cloth after PEI adsorption. Thus, when the cloth is washed with water, especially with buffer, the numbers of PEI molecules are greatly reduced.

The washed cloth is usually cross-linked with gluteraldehyde to activate enzyme coupling. Bahulekar et al. indicate that once treated with gluteraldehyde, gluteraldehyde-active aldehydes are fairly well removed from the PEI polymer backbone, and thus almost only gluteraldehyde aldehydes are available for enzyme immobilization. Therefore, with these methods not only is electrostatic enzyme attraction to support severely restricted, but also few reactive groups are available for actual enzyme immobilization. This likely limits the amount of enzyme immobilized and can make a lightly bound enzyme susceptible to detachment from the carrier.

The multilayer enzyme immobilization procedure of the present invention does not include a washing step after PEI adsorption on fibers to remove excess PEI. Therefore, in contrast to the "monolayer" enzyme immobilization procedure described above, the present invention provides for the formation of at least two layers of PEI-enzyme aggregates that at least partially and typically completely cover the fibrils, which aggregates are subsequently cross-linked with a fixative and then optionally washed with distilled water and acidic acid buffer solution. By forming two or more layers of PEI-enzyme aggregates, the present invention provides for increased enzyme immobilization yield as compared to monolayer enzyme immobilization procedure, wherein only a limited amount of PEI is adsorbed on the fibrous matrix.

Figure 5:
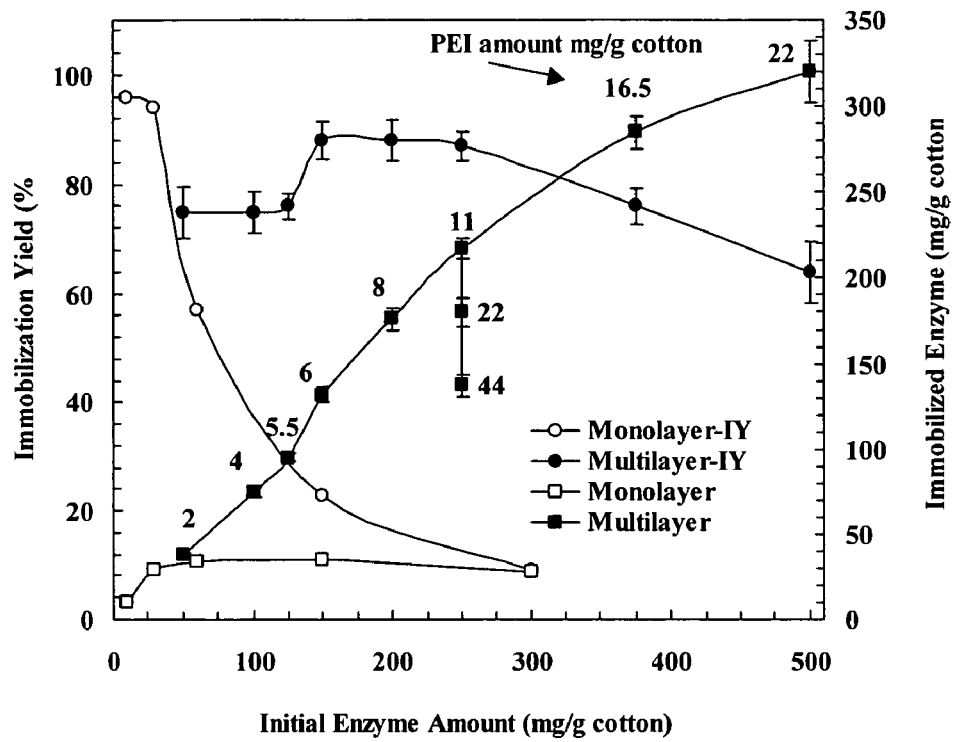
FIG. 5 is a graphical illustration of the effect of enzyme concentration on immobilization yields for multilayer and monolayer enzyme immobilization on cotton cloth, wherein 20 mg of PEI was used for the monolayer, and wherein a PEI to enzyme ratio of between about 1/22 and about 1/25 was used for the multilayer procedure.

Ratio of PEI to Enzyme. The ratio of PEI to enzyme can affect the level of immobilized enzyme that forms on the fibrous matrix, e.g., cotton cloth. As such, a wide range of PEI to enzyme ratios, from between about 1/5.7 and about 1/80, were investigated in the development of the present multilayer enzyme immobilization procedure. As noted herein, the amount of PEI can be anything so long as it can be dissolved in water. Therefore, any concentration of PEI and enzyme, up to their solubility in water, can be employed in accordance with the present invention, and their relative amount ca be adjusted with the volumes of PEI and enzyme solutions to be mixed. Typically, the ratio of PEI to enzyme is between about 1/33.3 and about 1/8.3. As shown in FIG. 5, increasing the amount of PEI per gram of cotton (e.g., from about 11 to about 44 mg for 250 mg enzyme) will result in a decrease in the immobilized amount (e.g., from about 218 to about 138 mg/g). Maximum enzyme immobilization is achieved when the PEI to enzyme ratio is between about 1/20 and about 1/25, and this ratio is consistent with the optimal ratio for the formation of PEI-enzyme aggregates. As also shown in FIG. 5, the amount of immobilized enzyme increases almost proportionally with the initial amount of enzyme in solution, up to 350 mg/g cotton at the ratio between about 1/22 and about 1/25. Under this condition, a relatively constant immobilization yield of 80–90% can be obtained. However, further increasing the enzyme amount above 350 mg/g cotton can reduce immobilization yield. Thus, a PEI to enzyme ratio of 1/22 at 250 mg enzyme per gram of cotton cloth is preferred.

Figure 6:
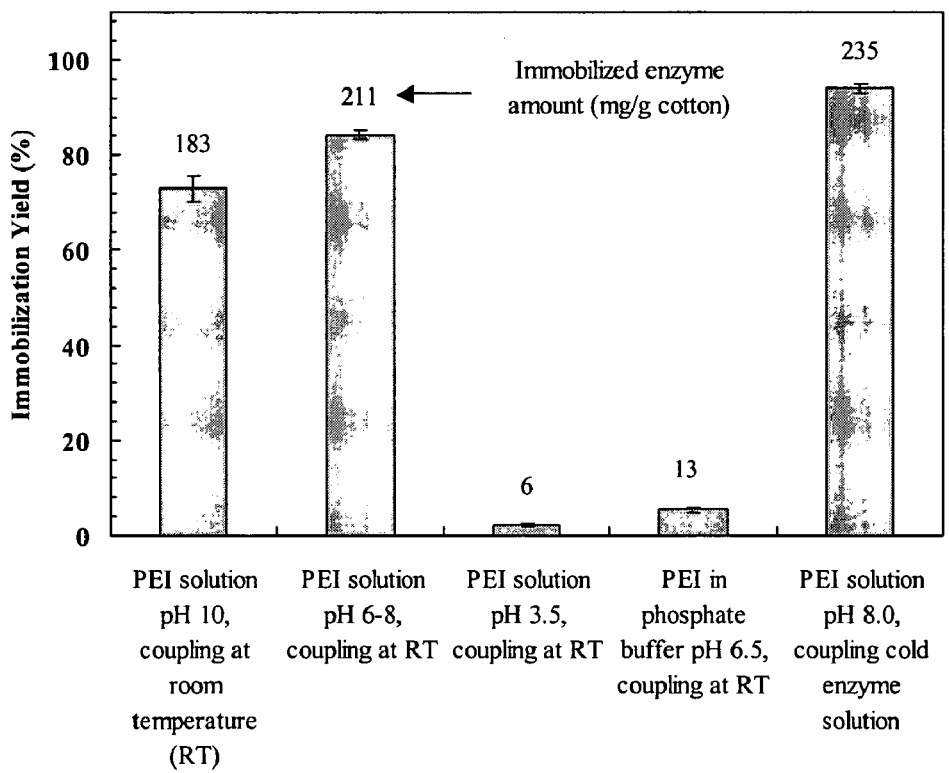
FIG. 6 is a graphical illustration of the effects of pH of PEI solution and enzyme coupling temperature during multilayer enzyme immobilization on cotton cloth.

Effect of pH and Temperature. As shown in FIG. 6, enzyme immobilization can also be affected by pH and temperature. In accordance with the present invention, the pH of the PEI and enzyme in solution can be between about 4 and about 10, depending upon the particular PEI and enzyme employed. Preferably, the pH is between about 6 and about 8. The final pH of the solution is determined by the initial pH of the solution and the concentration of reactants since no buffer is used in the preparation of the PEI and enzyme solutions. For example, a solution of 0.22% PEI has a pH value of between about 9.5 and about 10. When no pH adjustment is done to the PEI solution, the final pH of the PEI-enzyme cloudy solution is between about 8.2 and about 8.4. When the pH of PEI solution is adjusted to between about 6.0 and about 8.0 and the enzyme is dissolved in distilled water (pH 6.6), insignificant differences are observed in the immobilization yield. However, when the pH of PEI enzyme solution is reduced to 3.5, the solution will lose its cloudy appearance and very little enzyme will be immobilized.

As also shown in FIG. 6, when the PEI solution is prepared in 0.05 M phosphate buffer, very low immobilization yield is achieved. Accordingly, the PEI solution is typically prepared by using distilled water. Although not wishing to be bound by any particular theory, it is contemplated that phosphate ions bearing negative charges compete with enzyme for interacting with PEI and essentially block the formation of PEI-enzyme aggregates. In contrast, ions with positive charges would cover the enzyme and, consequently, PEI would not be able to reach or would be repelled by the enzyme. Since ionized buffer species are small compared with the enzyme, the immobilization capacity of PEI would be greatly reduced. Therefore, in accordance with the present invention, typically no buffer is used and the solution pH is typically maintained in the range of between about 6 and about 8 during the PEI-enzyme coupling reaction. Solution pH can be adjusted, when necessary, using HCl and/or NaOH solutions of sufficient molar concentration.

The temperature for PEI-enzyme immobilization can also affect the activity of immobilized enzyme. The temperature can be as high as 65° C. as long as the enzyme is not deactivated. Typically, the temperature is less than 50° C., and preferably less than 45° C. (more particularly between about 4 and about 25° C.). A preferred temperature range is between about 0° C. and room temperature. Here too, this will depend upon the particular enzyme employed. Although the temperature is not typically controlled during PEI-enzyme coupling, the enzyme solution is typically kept on ice or otherwise kept cold until it is added to the fibrous matrix that contains PEI. Cold enzyme solution (e.g., between about 0 and about 25° C.) produces a higher immobilized enzyme activity yield and more rapid enzyme immobilization (see FIG. 6). The cloudiness of the PEI-enzyme mixture will typically clear within 5 min., and over 95% of the activity associated with the initial enzyme solution is retained on the fibrous matrix, e.g., cotton cloth. Moreover, more reproducible results can be obtained when cold enzyme solution is used.

Cross-linking of PEI-enzyme Aggregates with Gluteraldehyde. As noted herein, in accordance with preferred embodiments of the present invention, the last step of the instant multilayered enzyme immobilization procedure is cross-linking the PEI-enzyme aggregates with enzyme fixative, e.g., gluteraldehyde. If no cross-linking is performed, most of the enzyme can leach out from the aggregates during enzyme activity determination (because of the presence of any buffer containing charged anions, e.g., acetate buffer). For instance, the presence of phosphate buffer (0.05 M) during gluteraldehyde cross-linking can reduce the yield of immobilization to about 10%. In accordance with the present invention, once the PEI-enzyme aggregates are coated on the fibrous matrix, (e.g., cotton cloth), the enzyme solution is decanted and an enzyme fixative solution is added to permanently fix the aggregates on the support. In addition, similar to the PEI-enzyme coupling reaction, the result of the cross-linking reaction appears to be also affected by temperature. The use of cold enzyme fixative solution tends to produce a higher final enzyme activity and more reproducible results. However, variations in the concentration (e.g., between about 0.05 and about 0.2% w/v) and pH (e.g., between about 6 and about 8) of the enzyme fixative solution and the reaction time (between about 5 and about 120 min) did not significantly affect the final activity of the immobilized enzyme. As noted herein, the enzyme fixative can be gluteraldehyde, formaldehyde, or any aldehyde or keto compound that can form covalent bonds with the amine groups of the enzyme protein. Application of a 0.1% gluteraldehyde solution for about 5 min. is typical.

Color of PEI-enzyme Coated Fibrous Matrix. The color of the fibrous matrix, i.e., cotton cloth, which is coated with multilayered PEI-enzyme aggregates, will typically remain white as normal, but can change to light yellow following cross-linking with gluteraldehyde or other enzyme fixatives. In experimental trials, a light yellow color was observed on the matrix within about 3 and about 5 min. of cross-linking, and there was no further change upon prolonged incubation. Although not wishing to be bound by any particular theory, the strength of the color (darkness) appears to be directly associated with the concentrations of enzyme fixative, PEI, and enzyme (i.e., the higher the concentrations of fixative, PEI, and enzyme, the darker the color). It appears that once the color is completely developed, the cross-linking reaction is complete and there is no further change (decrease or increase) in the final enzyme activity. Thus, one can use visual observation of color development to determine when the cross-linking reaction is substantially complete.

In order that the invention may be more readily understood, reference is made to the following examples, which are intended to illustrate the invention, but not limit the scope thereof. A fibrous-bed biocatalyst reactor for production of galacto-oligosaccharides from lactose is described and comprises multilayer immobilized enzyme prepared in accordance with preferred embodiments of the present invention. Other experimental procedures and results with respect to reaction kinetics are also discussed.

Example 1

Enzyme and Reagents. β-galactosidase from *A. oryzae* (fungal lactase activity 100,000 U/g) was obtained from Genencor International (Rochester, N.Y.). Each gram of the enzyme contained 100,000 fungal lactase units (FLU). One unit is defined as the amount of enzyme that liberates 1 μmol of o-nitrophenol from o-nitrophenyl-β-galactopyranoside (ONPG) per min at pH 4.5 and 37° C. (Genencor). Lactose (99.9%) from whey was from Brewster Dairy (Brewster, Ohio). Polyethyleneimine [PEI; $(C_2H_5N)_n$] as 50% (w/v) (number average molecular weight 60,000; average molecular weight 750,000) and glutaraldehyde as 25% (w/v) aqueous solutions were from Sigma (St. Louis, Mo.). Glacial acetic acid (Fisher) and sodium acetate trihydrate (J. T. Baker, Phillipsburg, N.J.) were used to prepare acetic acid buffer. Cotton terry cloth and nonwoven poly(ethylene terephthalate) (PET) fabrics were obtained locally. All solutions for PEI, gluteraldehyde, and enzyme were prepared with distilled water. The solution pH was adjusted, when necessary, using HCl or NaOH solution of sufficient concentration.

PEI-Enzyme Aggregate Formation. The procedures to form PEI-enzyme complex/aggregate by mixing PEI and enzyme in solution are illustrated in FIG. 1. Various amounts of PEI (0.15–0.60 mg in 0.1 mL of solution) were mixed with 1 mL of 5 mg/mL enzyme solution in microcentrifuge tubes to study the effect of PEI concentration (or the ratio of PEI to enzyme) on the formation of PEI-enzyme aggregates. After ~5 min, 0.1 mL of 0.2% gluteraldehyde solution was added to the mixture. The mixture containing PEI-enzyme aggregates was centrifuged at 10,000 rpm for 1 min. Initial enzyme activities associated with the PEI-enzyme slurry (containing gluteraldehyde) and supernatant were determined and compared with free enzyme (containing neither PEI nor gluteraldehyde). The morphology of PEI-enzyme aggregates in cloudy turbid slurry was analyzed with a light microscope.

Figure 2:
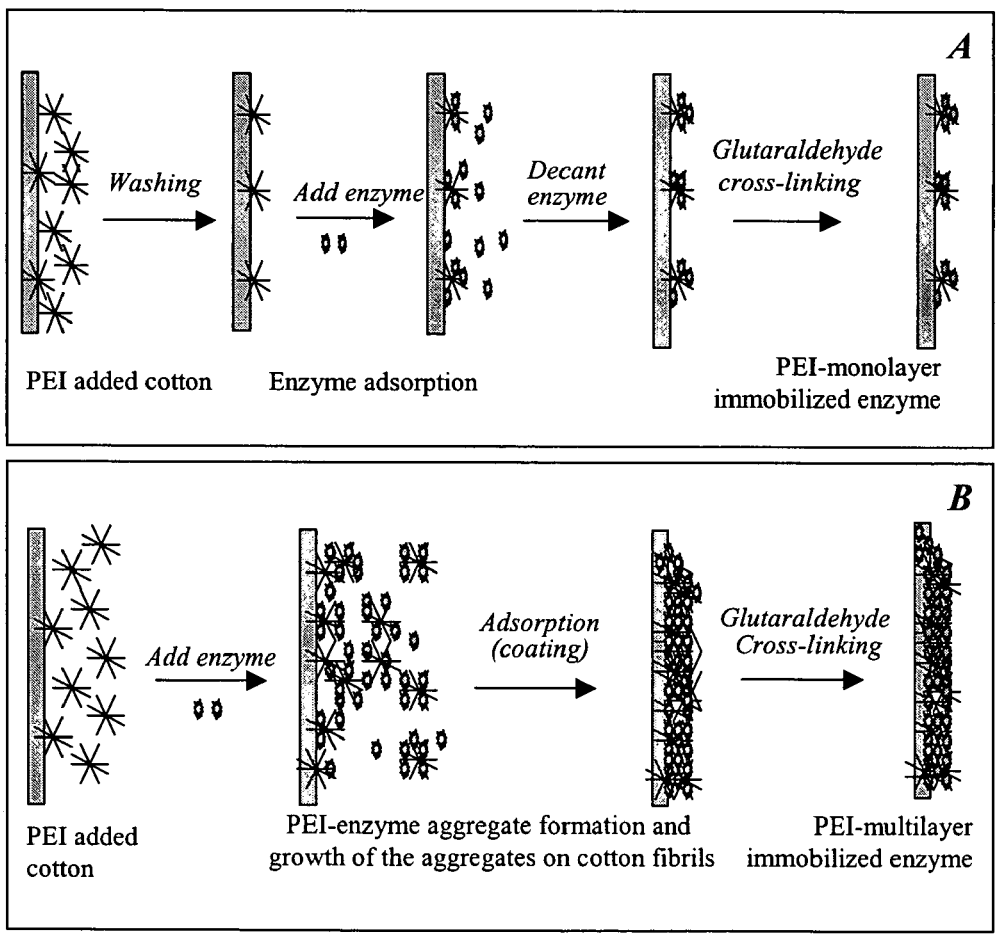
FIG. 2 is a schematic illustration of the procedure and proposed mechanisms for PEI-monolayer (A) and -multilayer (B) enzyme immobilization on cotton cloth.

Enzyme Immobilization on Cotton Cloth. The procedures for PEI-enzyme immobilization on cotton cloth are illustrated in FIG. 2. Enzyme immobilization on cotton cloth involved three main steps: adsorption of PEI solution to cotton cloth, introduction of enzyme to PEI-containing cloth, and gluteraldehyde cross-linking of PEI-enzyme aggregates coated on the cotton. The cross-linked, PEI-immobilized enzyme aggregates on cotton cloth were washed extensively with distilled water and then with acetic acid buffer (0.1 M, pH 4.5). The solutions were kept cold on ice right until use. The treated cotton cloth with immobilized enzyme was stored in the buffer (0.1 M, pH 4.5) and refrigerated until use. All procedures were carried out in 125-mL Erlenmeyer flasks, and incubations were performed in a shaker-incubator (Lab-Line) at 150 rpm at room temperature. Two procedures were developed. The first also involved washing after PEI adsorption and thus produced "monolayer" enzyme immobilization on the cotton fibrils. The second procedure did not wash after PEI coating and thus produced "multilayer" enzyme immobilization. More details are given below.

Monolayer Immobilization. The method was a modification of the procedure developed by Yamazaki et al. for invertase (see Yamazaki et al. Immobilization of invertase on polyethyleneimine-coated cotton cloth. *Biotechnol. Lett.* 1984, 165–170). A large volume of PEI solution (50 mL/g cotton cloth) was allowed to adsorb to cotton cloth for 2 h. After adsorption, cotton cloth was extensively washed under running distilled water to remove excess PEI from the cotton. The washed cloth was blotted between paper towels and was soaked in enzyme solution for 2 h. Enzyme-adsorbed cotton was then cross-linked with 2% gluteraldehyde for 2 h.

Multilayer Immobilization. Unless otherwise noted, 1 mL of PEI solution (pH 8.0) containing 2.2 mg of PEI was added to each 0.2 g piece of cotton cloth. The solution volume was at a sufficient level to completely wet the cloth, thereby allowing a homogeneous distribution of PEI to the matrix. After adsorption of PEI, 50 mg of enzyme (10 mL of 5 mg/mL enzyme solution) was added. Upon the addition of enzyme to PEI-adsorbed cotton, a "milky" turbid solution was formed. The flasks were put into a shaker-incubator for 5–10 min. Within 5 min, the white turbidity disappeared and the coupling solution was completely clarified. The clarified coupling solution was slowly decanted and PEI-enzyme-coated cottons were immersed in a cold gluteraldehyde solution (0.2% (w/v), pH 7.0) for cross-linking for 5 min. The cross-linked, PEI-immobilized enzyme aggregates on cotton cloth were washed extensively with distilled water and then acetic acid buffer (0.1 M, pH 4.5). It is important to note that unlike the monolayer immobilization procedure described directly above, in the multilayer enzyme immobilization procedure of the present invention, there is no washing step until the completion of gluteraldehyde cross-linking.

Example 2

Figure 3:
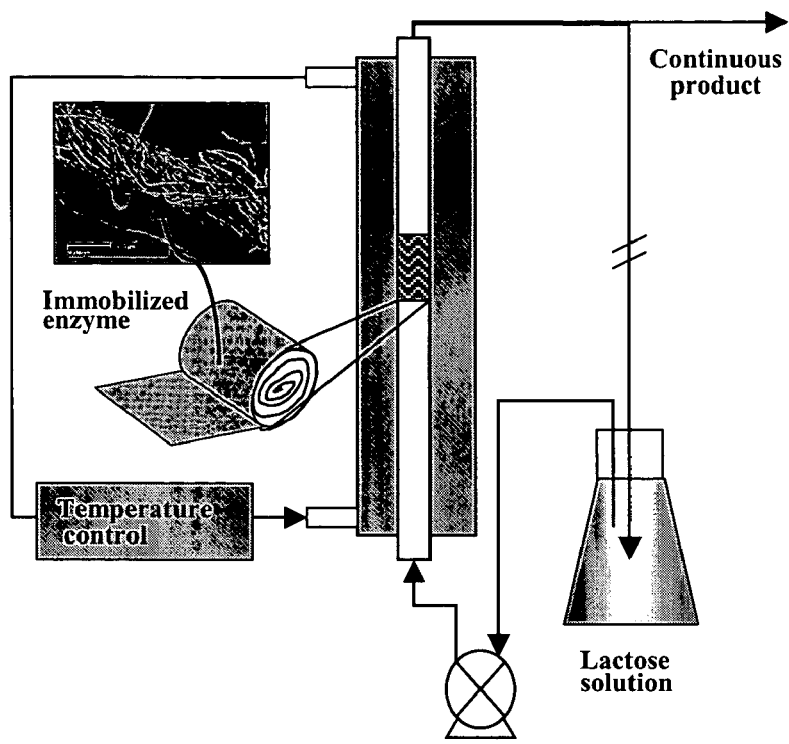
FIG. 3 is a schematic diagram of the immobilized enzyme cotton cloth reactor described herein.

Reaction Kinetics. GOS formation kinetics with immobilized enzyme was studied in a recycle batch packed-bed reactor (FIG. 3). A small piece of cotton cloth that contained immobilized PEI-enzyme aggregates (~0.4 g) was placed in the glass column reactor (i.d. of 9 mm) with a water jacket maintained at a constant temperature (40° C., unless otherwise noted). The lactose solution in the flask (total solution volume, ~85 mL) was continuously recirculated through the immobilized enzyme reactor at a high flow rate of 90 mL/min. The lactose solution was prepared by dissolving lactose in 0.1 M acetic acid buffer (pH 4.5, unless otherwise noted). Samples (100 µL or 0.1 mL) were taken from the flask at appropriate time intervals and analyzed for sugar contents by high performance liquid chromatography (HPLC). The reaction kinetics was studied at 400 g/L lactose solution for three different levels of enzyme loading (35, 130, 240 mg enzyme/g cotton), four different pH values (4.15, 4.5, 6.0, 6.5), and two temperatures (40, 50° C.).

GOS formation kinetics of PEI-enzyme aggregates and free enzyme was also investigated under similar conditions. To prepare aggregates in solution, PEI solution (1 mL, 0.22% w/v, pH 8.0) was mixed with 10 mL of enzyme solution (5 mg/mL) and incubated for 10 min. After incubation, 1 mL of gluteraldehyde solution (0.2% w/v) was added and the incubation was continued for 5 min. The solution (~12 mL) containing PEI-enzyme aggregates was added to 50 mL of lactose solution (440 g/L in 0.1 M acetic acid buffer, pH 4.5) in 125-mL Erlenmeyer flasks, and the reaction was carried out at 40° C., 250 rpm in a shaker-incubator. For control, a free enzyme solution that contained just distilled water was used instead of PEI and gluteraldehyde solutions, and the same conditions were used for GOS formation. Samples (0.1 mL) were drawn from the reaction mixtures at appropriate time intervals and added to 0.9 mL of distilled water at 95° C. to stop the enzyme activity. The sugar contents were analyzed by HPLC.

Stability of Immobilized Enzyme. The thermal stabilities of PEI-immobilized enzyme in 0.1 M acetate buffer (pH 4.5) at various temperatures (40, 50, and 60° C.) were studied in a single-pass continuous reactor (see FIG. 3). Cotton cloth immobilized enzyme at the level of 250 mg/g was used for 50 and 60° C., and 150 mg/g was used at 40° C. The reactor was continuously fed with a lactose solution (100 g/L in 0.1 M acetic acid buffer, pH 4.5) at a constant flow rate (100 mL/min) and temperature for a necessary period. Samples from the reactor effluent were collected at proper time intervals and analyzed by HPLC.

GOS Production in Continuous Reactor. Continuous production of GOS from lactose was studied in a single-pass reactor (FIG. 3). Approximately 0.72 g of cotton cloth containing immobilized PEI-enzyme aggregates was placed in the column reactor (i.d. of 9 mm) with a total packed bed length of ~3.5 cm (the bed volume was ~2.23 mL). Continuous production of GOS from lactose with the reactor was studied at 40° C. to evaluate the reactor long-term performance. The reactor was fed with 400 g/L lactose solution (0.1 M acetic acid buffer, pH 4.5) for about 3 days. The lactose solution was kept in a 60° C. waterbath to prevent crystallization of lactose. The feed rate was changed in the range of 140 and 160 mUh so that near and at 50% lactose conversion the maximum GOS content could be obtained in the product stream. When the feed rate was changed, at least 4–5 bed volumes were fed to allow the reactor to reach steady state. Samples from the reactor effluent were then collected at proper time intervals and analyzed by HPLC.

Example 3

Scanning Electron Microscopy (SEM). Fibrous matrix samples were dried in a critical point dryer. After being sputter-coated with gold/palladium, the samples were examined using a scanning electron microscope (Philips XL-30).

Analytical Methods. Enzyme Activity Assay. The activity of cotton cloth immobilized enzyme made in accordance with an embodiment of the present invention was measured with 100 g/L lactose as the substrate in 0.1 M acetic acid buffer (pH 4.5) at 40° C. in a shaker-incubator at 450 rpm for about 5 min. After incubation, the cloth was removed from the reaction mixture and a volume of sample taken and mixed at one-to-one ratio with 0.1 N NaOH to inactivate possible free enzyme activity leached during activity determination. The glucose concentration in the sample was determined with a glucose analyzer (YSI 2700 Select, Yellow Springs, Ohio). The activity of the immobilized enzyme was determined by direct comparison of the reading with the standard curve in the plot of glucose concentration versus enzyme activity times the reaction time [g/L vs (mg/mL) ·min] obtained from free-enzyme reactions and then used to estimate the amount of active enzyme (mg/g cotton) and immobilization yield (%).

HPLC Analysis. The concentrations of sugars in sample solutions (glucose, galactose, lactose, and galacto-oligosaccharides) were determined by HPLC. An HPLC system consisting of a pump (Waters 6000A), an autosampler (Waters WISP 710B), a carbohydrate analysis column (Phenomenex, Rezek RNM carbohydrate column, 7.8 mm×150 mm), a column heater (BioRad), a refractive index detector (Waters 410 differential refractometer), and a Shimadzu CLASS-VP chromatography data system (version 4.2 integrator) was used. The eluent was pre-degassed distilled water (at 85° C.) at a flow rate of 0.4 mL/min. Distilled water was degassed by first boiling and then sonicating for 30 min. The column temperature was maintained at 85° C., and the detector temperature was set at 45° C. The concentrations (w/v) of these sugars (e.g., lactose, glucose, galactose, and oligosaccharides including tri-, tetra-, and pentasaccharides) should be proportional to their peak areas with the same proportionality constant. Thus, the normalized sugar concentrations, presented as weight percentages of total sugars, were determined from peak heights and are reported herein.

Figure 7:
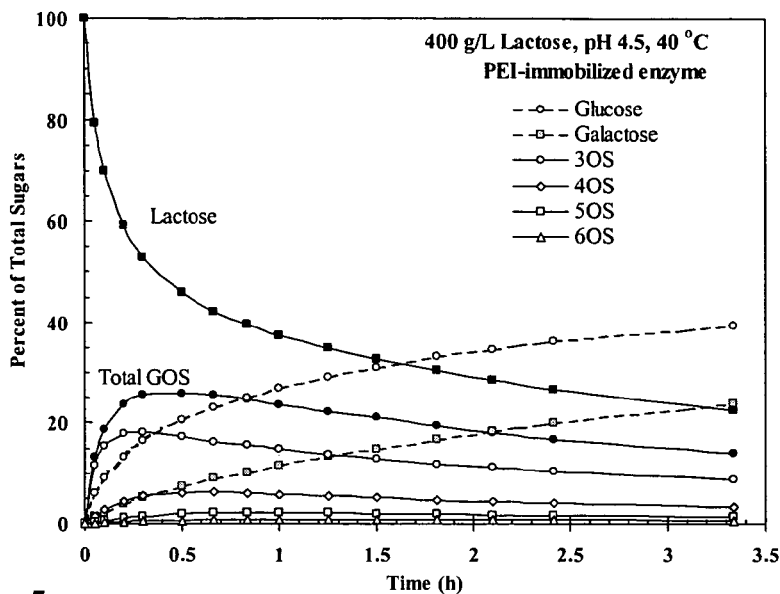
FIG. 7 is a graphical illustration of the reaction kinetics of lactose hydrolysis and galacto-oligosaccharide formation catalyzed by PEI-immobilized enzyme in a recycle batch reactor at 40° C. with an initial lactose concentration of 400 g/L.
Figure 8:
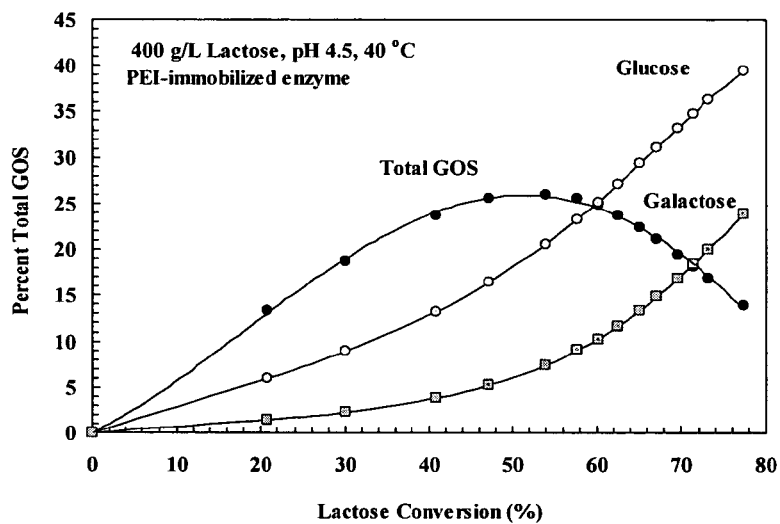
FIG. 8 is a graphical illustration of the kinetics of galacto-oligosaccharide formation as affected by lactose conversion catalyzed by PEI-immobilized enzyme in a recycle batch reactor at 40° C. with an initial lactose concentration of 400 g/L.
Figure 8:
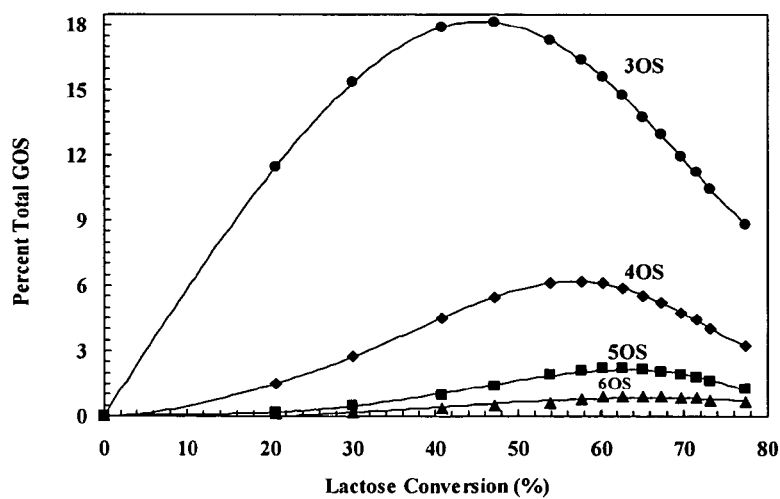

Galacto-oligosaccharide Formation Kinetics. GOS formation kinetics from lactose with the multilayered PEI-immobilized enzyme was studied in packed-bed reactors. FIG. 7 shows typical reaction kinetics for lactose hydrolysis and GOS formation. In general, a high rate of initial GOS formation was accompanied with rapid decrease in lactose concentration. As reactions continued, GOS formation leveled off and then decreased while glucose and galactose continued to increase. The amount of galactose produced from lactose hydrolysis was less than that of glucose because galactose was also used to form GOS. FIG. 8 shows that the GOS production kinetics as affected by lactose conversion, defined as conversion of lactose to the other sugars. As seen, a maximum GOS production was obtained at ~50% lactose conversion. As also shown in FIG. 8, the GOS produced from the reaction was primarily composed of trisaccharides (3-OS). Larger GOS such as tetra- and pentasaccharides were produced at lower levels, and their production peaked at higher lactose conversions, suggesting successive conversions to higher oligosaccharides (from 3-OS to 4-OS and then to 5-OS, etc.). At 50% lactose conversion where the total GOS peaked, the proportions of tri-, tetra- and penta-oligosaccharides were approximately 70%, 25%, and 5% of total GOS formed, respectively.

Figure 9:
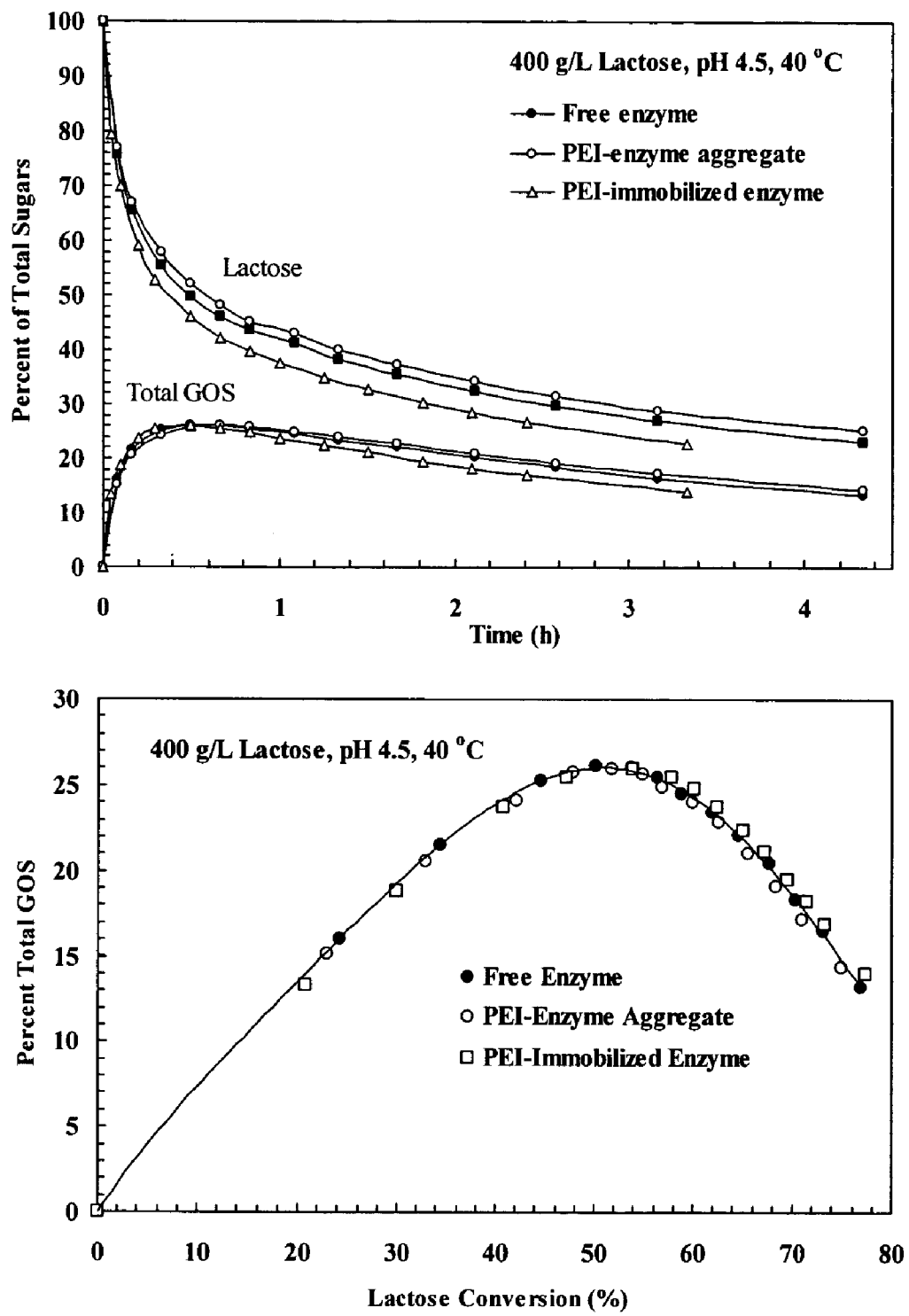
FIG. 9 is graphical illustration of comparisons of galacto-oligosaccharide formation during lactose hydrolysis catalyzed by free enzyme, PEI-enzyme aggregates in solution, and PEI-immobilized enzymes on cotton cloth in a recycle batch reactor.

Effect of PEI-immobilization on Reaction Kinetics. Although the activity of the enzyme was not impaired (FIG. 4) upon formation of relatively large PEI-enzyme aggregates (10–50 µm in diameter), this might impose severe mass transfer limitation under the conditions of GOS production. Because of the viscosity of the lactose solution, formation of GOS products larger in size and simultaneous release of small monosaccharides known to be inhibitory to the enzyme, mass transfer limitations could cause significant reduction in GOS formation. The high lactose concentrations (~400 g/L) and lactose conversion (~50%) were used to favor GOS formation, which might not work as well with the large enzyme aggregates. There would be significant internal mass transfer resistance introduced upon aggregation of the enzyme with PEI. Similarly, the PEI-enzyme aggregates coated on the surface of cotton also could impose severe diffusion limitation. Nevertheless, as shown in FIG. 9, the reaction kinetics of PEI-enzyme aggregates was unchanged as compared to the soluble enzyme reaction. The amounts of GOS formed at various lactose conversions were the same for all three systems studied (PEI-immobilized enzyme, free enzyme, and PEI-enzyme aggregate). Almost identical curves for lactose hydrolysis and GOS formation were observed for PEI-enzyme aggregate and free enzyme; both had about the same amount of enzyme (1 mg/mL) in the reaction medium. A slightly faster reaction rate was obtained with PEI-enzyme immobilized on cotton (240 mg/g cotton) in the packed bed reactor because there was more enzyme present in the reaction medium. Thus, not only was the catalytic activity preserved, but also the GOS formation characteristics, indicating that the PEI-enzyme aggregates were highly porous and permeable and did not impose any adverse effect caused by diffusion.

Figure 10:
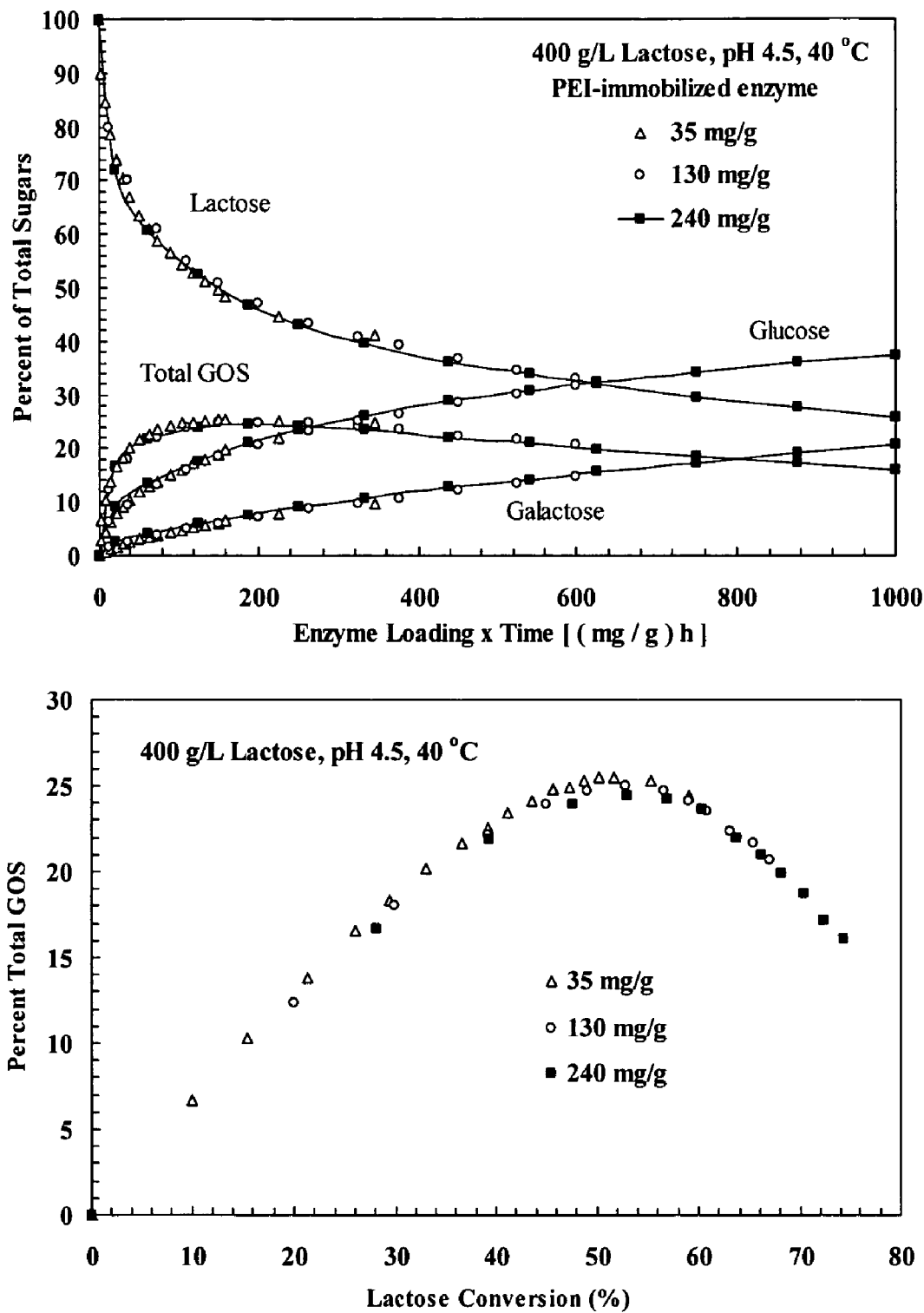
FIG. 10 is a graphical illustration of the kinetics of lactose hydrolysis and galacto-oligosaccharide formation catalyzed by PEI-immobilized enzyme at three different enzyme loadings (35, 130, and 240 mg/g cotton)

It was also found that the reaction kinetics and GOS formation were not affected by the enzyme loading (FIG. 10). As the enzyme loading increased (35, 130, and 240 mg/g cotton), the GOS productivities also increased proportionally (data not shown). It is important to point out that 1 g of cotton cloth occupies only 2–5 mL reactor volume, depending on the packing density. Therefore, with the cotton cloth immobilized enzyme, a working enzyme concentration of more than 100 mg/mL (240 mg/g cotton in 2–5 mL reactor volume) can be achieved, which is 100-fold higher than a free enzyme concentration of, for example, 1 mg/mL. It should be noted that even at this high level of enzyme loading, PEI-immobilized enzyme produced as much GOS as soluble enzyme did. Therefore, a high volumetric productivity, which is a major factor affecting the production cost, can be achieved with a high enzyme loading without suffering from any loss in GOS production due to diffusion limitations.

Figure 11:
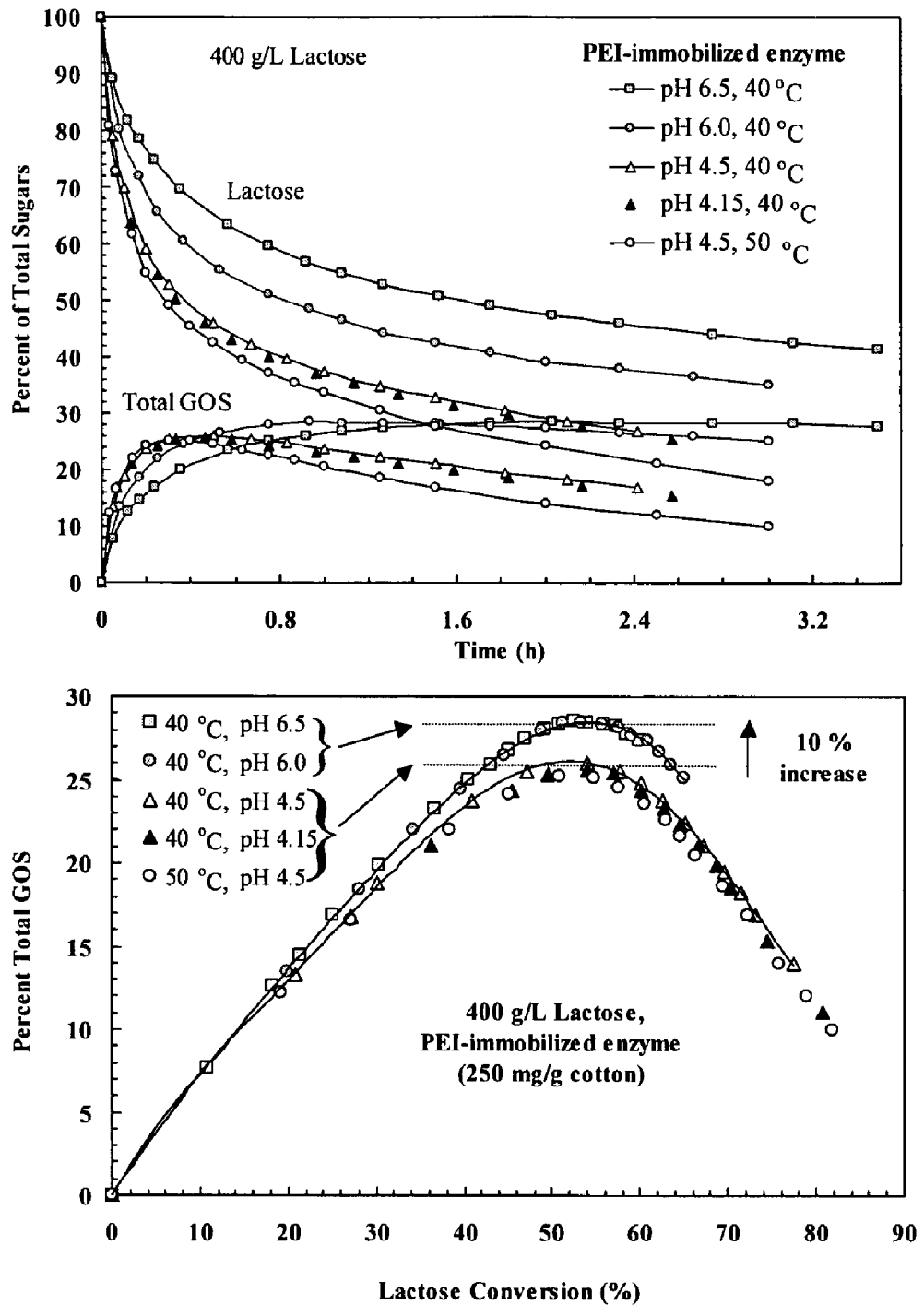
FIG. 11 is a graphical illustration of the effects of pH and temperature on galacto-oligosaccharide production during lactose hydrolysis catalyzed by PEI-immobilized enzyme in a recycle batch reactor.

Effects of pH and Temperature on GOS Formation. Although temperature and pH normally affects the reaction rate, they have been found to have negligible effects on GOS content. Since the most likely substrates for industrial GOS production are sweet and acid whey and whey permeate, the effects of pH (~4.5 and ~6.0) and temperature (40 and 50° C.) on GOS formation were investigated. As shown in FIG. 11, a higher rate of GOS formation was obtained at pH 4.5 and 50° C., compared with lower temperature and higher pH, which was consistent with our expectation. However, there was ~10% increase in the GOS content produced at higher pHs (6.0 or 6.5). In all other systems that previously had been studied, a change in the reaction pH did not affect the level of GOS formation. Iwasaki et al., using soluble β-galactosidase from *A. oryzae*, reported that pH had no effect on GOS formation at 400 or 500 g/L lactose concentration in the tested pH range of 3–7 (see Iwasaki et al. Galacto-oligosaccharide production from lactose by an enzymatic batch reaction using β-galactosidase. *Process Biochem.* 1996, 31, 69–76). We have also found previously with a covalent immobilization of this enzyme that pH had no effect. Therefore, the observed effect on GOS formation was likely caused by the PEI immobilization method, which influenced the characteristics of the immobilized enzyme and yielded a change in the product profile (more synthesis over hydrolysis). PEI enzyme immobilization involves electrostatic complex formation between negatively charged enzyme and positively charged PEI. The immobilized enzyme cross-linked within the PEI matrix is thus more likely to respond to changes in the pH. Consequently, there might be a significant change in the shape and/or the charge of the active site of the enzyme at pH 6–6.5, which resulted in an active site that favored more synthesis over hydrolysis.

Figure 12:
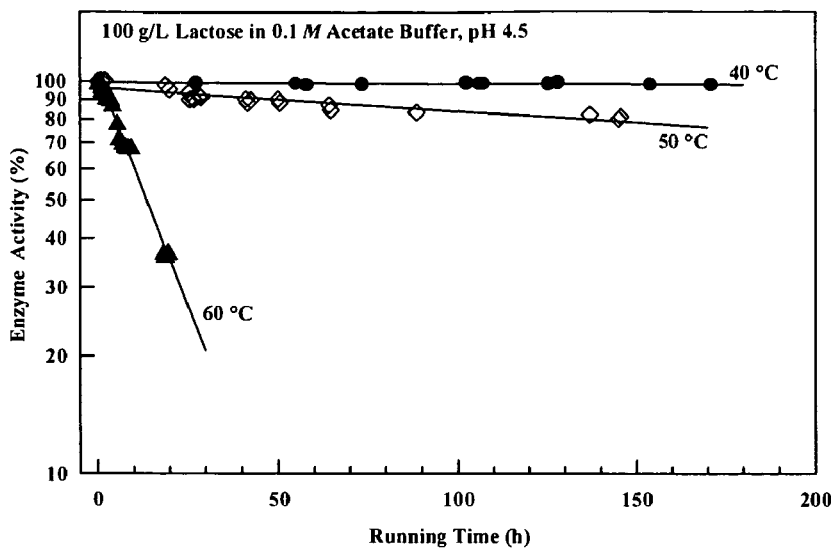
FIG. 12 is a graphical illustration of thermal deactivation of PEI-immobilized enzyme on cotton cloth at various temperatures.

Thermal Stability. The thermal deactivation of the PEI-immobilized enzyme over time at various temperatures was studied to evaluate the thermal stability of the immobilized enzyme. As can be seen in FIG. 12, thermal deactivation of immobilized enzyme followed first-order reaction kinetics. The deactivation rate constants (kd) were determined from the slopes of these semilogarithmic plots and then used to estimate the half-lives of the enzyme at various temperatures, which are listed in Table 1. PEI-immobilized enzyme had an estimated half-life of close to 1 year at 40° C. and 21 days at 50° C. The increase in the deactivation rate constant kd with temperature followed the Arrhenius relationship, and the activation energy Ea was higher for the immobilized enzyme (Ea=274 kJ/mol) than free enzyme (Ea=228 kJ/mol). Compared to free enzyme, the immobilized enzyme was 10- to 20-fold more stable.

TABLE 1

Comparison of Thermal Stabilities of Free and Immobilized Enzymes[a]

| | free enzyme[b] | | PEI-immobilized enzyme[c] | |
|---|---|---|---|---|
| temp (° C.) | $K_d$ ($h^{-1}$) | half-life (h) | $K_d$ ($h^{-1}$) | half-life (h) |
| 40 | 0.0017 | 399 | 0.000086 | 8073 |
| 50 | 0.0141 | 49 | 0.001370 | 505 |
| 60 | 0.3325 | 2 | 0.048200 | 15 |

[a]The deactivation rate constant $k_d$ was determined from experimental data, which followed a first-order reaction kinetic model. The enzyme half-life was calculated from the $k_d$ value.
[b]Incubated in pH 4.5 acetate buffer; activity was determined at various intervals.
[c]Immobilized enzyme in packed-bed reactor.

The stabilization effect of enzyme immobilization on PEI composites may be attributed to several mechanisms: (I) The motion of protein chain segments is restricted through attachment to PEI, and individual contact of enzymes is restricted. (II) As a result of charges of enzyme and PEI, the immobilized enzyme is well hydrated, and protein denaturing segmental collisions are unlikely. (III) Since enzyme is embedded in PEI, access by proteases is blocked. (IV) Access of hydrophobic molecules is restricted from the aggregate as a result of hydrophilicity of the system. However, the stabilization effect of the ionic immobilization of enzyme varies with the type of enzymes. For instance, glucose oxidase and lipase were immobilized by the same method using PEI, yet the latter was stabilized much more. It should be noted that the PEI-immobilized enzyme also had good stability under dehydration conditions. Upon drying the cotton cloth with PEI-immobilized enzyme for 2 days at room temperature, only 17% decrease in the enzyme activity was observed after rehydration. It was indicated that drying might induce nonspecific interactions of enzyme and polyelectrolyte yielding denaturation. Thus, the immobilized enzyme may be dried and stored at room temperature for a long period of time before use.

Figure 13:
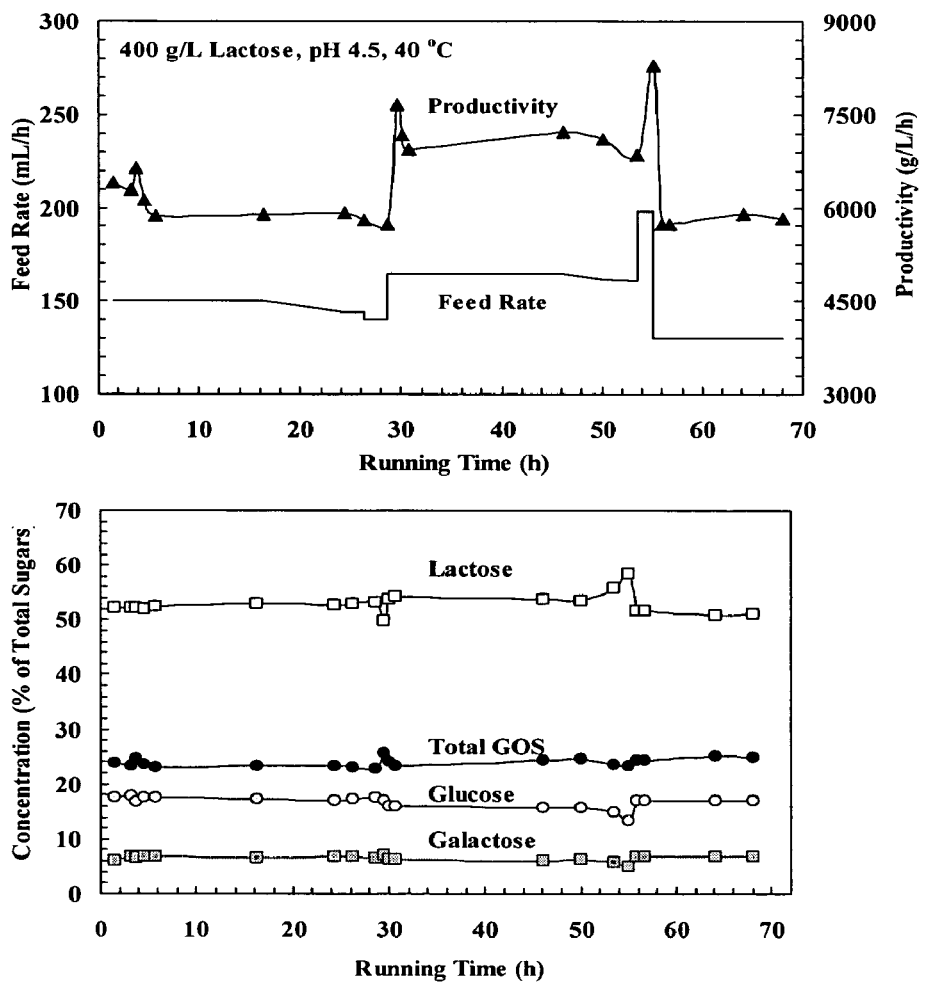
FIG. 13 is a graphical illustration of continuous production of galacto-oligosaccharides by PEI-immobilized enzyme on cotton cloth packed in a single-pass reactor operated at 40° C. with 400 g/L lactose in the feed solution.

Continuous Reactor. FIG. 13 shows the production of GOS from lactose in the continuous reactor with PEI-immobilized enzyme at a loading of 250 mg/g cotton at 40° C. Other than the effect caused by changes in the feed rate, the reactor performance was stable and there was no apparent decrease in the level of GOS or lactose conversion during 3 days' continuous run. Because of a very low amount of immobilized enzyme (0.72 g) and high feed rate (150–160 mL/h), effluent was very sensitive to the change in the flow rate. At ~150 mL/h feed rate, about 47% lactose conversion was attained and the outlet product stream contained 23–24% (w/w) GOS with a reactor productivity of ~6000 g/L/h, which was calculated from the final GOS concentration (g/L) times the feed rate and divided by the reactor volume (~2.23 mL). In general, the change in feed rate resulted in a greater change in the reactor productivity while GOS content remained within 1% or 2% variation, which is the case near 50% lactose conversion as can be seen in the kinetics shown in FIGS. 8 and 9. When the feed rate increased to 165 mL/h, lactose conversion slightly decreased to 45–46% with more or less the same GOS content while productivity increased to 7000 g/L/h. When the feed rate decreased to 135–140 mL/h, 50% lactose conversion was obtained with 25.8% GOS in the final product and reactor productivity of 5800–6000 g/L/h.

Factors Affecting PEI Enzyme Immobilization. PEI forms ionic complexes with macromolecules containing acidic domains leading to water-soluble and -insoluble complexes, and this behavior is affected by salt concentration, pH, and the concentration of precipitable components. To enhance effective complex formation with PEI, polyaspartic acid tails were fused to glucoamylase and β-galactosidase. The more negatively charged the enzyme is, the less the amount of PEI necessary for complex formation. Caruso and Schuler studied the effect of enzyme complexation on its activity in solution and found that glucose oxidase or peroxidase that was precomplexed with oppositely charged polyelectrolyte (enzyme-to-polymer mass ratio of 1:10) in solution had 60–70% less activity than the corresponding free enzymes (see Caruso et al. Enzyme multilayers on colloid particles: Assembly, stability and enzymatic activity. Langmuir2000, 16, 9595–9603). In accordance with the present invention, although large macroscopic sizes of PEI-enzyme aggregates were formed, the activity of the enzyme was not impaired. Intact catalytic activity even after gluteraldehyde crosslinking suggested that the PEI enzyme aggregates were highly porous and permeable to lactose and GOS.

In accordance with the present invention, a multilayered enzyme immobilization procedure was developed by eliminating the washing step after PEI adsorption on fibers. Besides the cotton cloth in the knitted form, various types of fibrous materials with different physical (e.g., knitted, nonwoven) and chemical characteristics, including poly(ethylene terephthalate) (PET) and rayon (restructured cellulose) were also investigated following the same procedure described before for cotton cloth. It was found that the enzyme immobilization yields achieved were similar to that of cotton cloth (Table 2). For instance, similar to cotton cloth, the optimum PEI to enzyme ratio of 1/22 was obtained using nonwoven PET fabric with 77% immobilization yield (220 mg/g PET). However, when PEI-coated PET fabric was washed (monolayer method) before enzyme addition, almost no immobilization of enzyme was achieved. With cotton, on the other hand, about 25–30 mg/g was obtained when cotton was washed after PEI adsorption. This indicated that cotton either retained more PEI or adsorbed PEI more strongly than PET. The difference could be attributed to the smoothness and hydrophobicity of PET surface compared with cotton. Similarly, Isgrove et al. reported that nylon having a hydrophobic and smooth surface was not good for enzyme immobilization and they thus applied an acid hydrolysis to increase surface roughness before PEI adsorption (see lsgrove et al. Enzyme immobilization on nylon's optimization and the steps used to prevent enzyme leakage from the support. Enzyme Microb. Technol. 2001, 28, 225–32).

Figure 14:
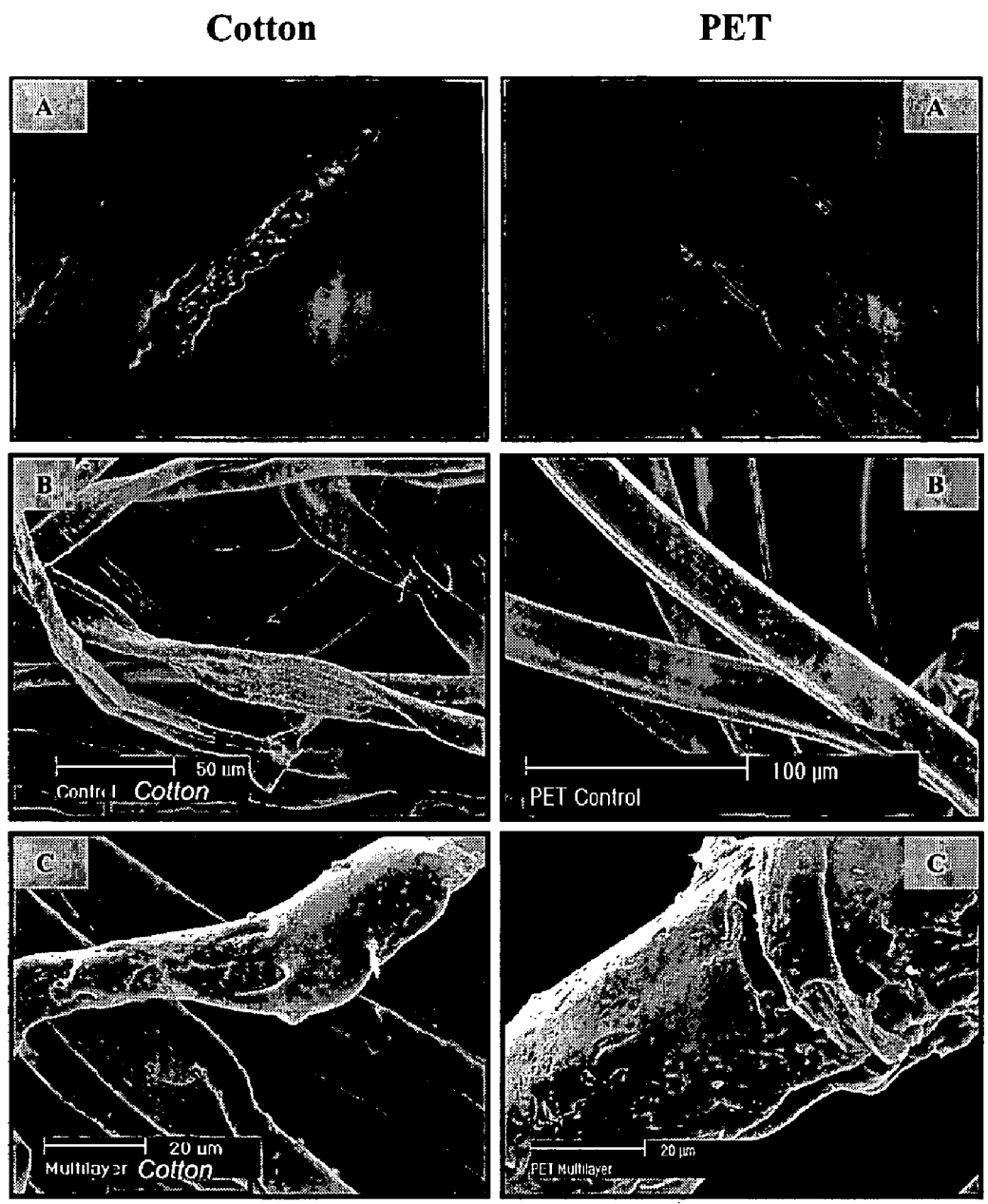
FIG. 14 shows a series of fibril micrographs of knitted cotton cloth and nonwoven poly(ethylene terephthalate) (PET) fabrics containing PEI-multilayer immobilized enzyme (250 mg enzyme and 12 mg PEI per gram of fabric) seen under a light (A) and scanning electron microscope (SEM) (C) as compared with SEM image for control fibrils (B).

Surface characteristics of multilayer immobilized enzyme on cotton cloth and PET fabrics were studied under a light microscope and by scanning electron microscopy. As can be seen in FIG. 14, the fibril surfaces of both cotton and PET fibers treated with the multilayered PEI enzyme immobilization were heavily (entirely) coated with layer(s) of PEI-enzyme aggregates. It is noted that the surface characteristics of PET and cotton fibers are quite different, as can be seen from the images of the untreated fibers. PET fibers had a smooth surface and were thicker in diameter and round shaped, while cotton cloth had rough surface with a flattened and twisted ribbon shape. It should be noted that the cracks or flacks seen especially in the coat of PET fiber were due to drying applied prior to SEM imaging. SEM imaging of PEI-monolayer immobilized enzyme on cotton cloth was no different from the untreated control samples. It is noted that the phenomenon of multilayered PEI enzyme immobilization relies more on the three-dimensional association of aggregates leading to growth and ultimately coating on the fibril surfaces of the fibrous matrix rather than just a formation of PEI-enzyme aggregate in solution. The driving force of the growth of aggregates appears to be dependent on a critical ratio of PEI to enzyme, yet the actual course of events is rather difficult to elucidate.

Comparisons to Other Studies. Table 2 shows the comparison between various fibrous matrices used for immobilization of several enzymes. Kamath et al. found that optimum enzyme (urease) loading was about 20 mg/g cotton flannel cloth. The activity yield was 43% when the PEI cloth adsorbed enzyme cross-linked with 1,1-carbonyldiimidazole, while only 7% activity was obtained when gluteraldehyde was used (see Kamath et al. Urease immobilized on polyethyleneimine cotton cloth. Appl. Biotechnol. 1988, 19, 251–8). Vol'f et al. used several different types of fibers and enzymes for therapeutic applications (see Vol'f et al. Immobilization of enzymes on fibrous supports. Prikl. Biokhim. MikrobioL 1986, 22, 664–8). Most of these procedures required several steps for activation or modification of the fiber before immobilization. It was found that the results of enzyme immobilization depended on the type of the fibrous supports and ranged from 10 to 90% immobilization yield. Apparently, multilayer enzyme immobilization produced higher activities and shorter immobilization time than most of the other methods reported. It should be noted that there was no prior activation necessary for this method. Recently, Kawai et al. described a novel multilayered immobilization procedure for aminoacylase in porous hollow-fiber support (see Kawai et al. High conversion in a symmetric hydrolysis during permeation through enzyme-multilayered porous hollow-fiber membranes. Biotechnol. Prog. 2001, 17, 872–75). The method was based on grafting of polymer chains containing epoxy group on hollow-fiber membrane by radiation-induced graft polymerization. An amount of 200 mg enzyme per gram of hollow fiber was introduced at 95% coupling yield (5% of the immobilized enzyme leached after gluteraldehyde cross-linking). The multilayer was composed of about 15 layers of enzyme. The yield they indicated was based on protein efficiency; the activity of immobilized enzyme was not measured.

Table 3 compares the reactor productivity and the maximum GOS content in the final product achieved in various studies reported in the literature. The productivity obtained from multilayered PEI-immobilized enzyme was much higher (50–100 fold) than those previously reported. β-galactosidase is one of the most commonly used enzymes and is widely available in large quantities. Axelsson and Zacchi performed economic evaluation of lactose hydrolysis by *A. oryzae* β-galactosidase (see Axelsson et al. Economic evaluation of the hydrolysis of lactose using immobilized β-galactosidase. Appl. Biochem. Biotechnol. 1990, 24/25, 679–93). It was found that when considering the use of free enzyme, the cost for the enzyme increases with increasing enzyme concentration in reaction mixture. The cost for soluble enzyme constitutes about 30% of the total cost at the optimal loading of 60 mg/L. When the enzyme was immobilized in alginate beads with carbodiimide crosslinking [1-ethyl-3-(3-dimethylaminopropyl)carbodiimide], the cost was about 10% of the total cost for the immobilized enzyme at the optimal loading of 5000 mg/L in a plug-flow tubular reactor (PFTR). The effectiveness factor was the lowest on PFTR compared to that of batch or controlled stirred tank reactor (CSTR). This is probably due to a diffusion effect in alginate beads where enzyme was encapsulated. In the present invention, 100–200 mg enzyme can be included per milliliter of the reactor volume, which means 2- to 4-fold more enzyme loading can be introduced with a linear increase in productivity. Also, with the use of cotton fabric, the immobilized enzyme functions as well as the free enzyme. Thus, much higher productivities and in turn much lower product cost can be realized.

TABLE 2

Comparison of Various Types of Fibrous Matrices and Enzyme Immobilization Methods

| fibrous matrix | means of activation and/or immobilization | enzyme | enzyme coupling time (h) | enzyme coupling amount (mg/g) | immobilization yield (%) | reference |
|---|---|---|---|---|---|---|
| amphoteric polycaproaminde fiber | gluteraldehyde | papain | 24 | 30 | 23 | 55[1] |
| aldehyde containing poly(vinyl alcohol) | gluteraldehyde | papain | 3 | 77 | 88 | 55[1] |
| regenerated cellulose fibers | dye direct white | papain | 0.4 | 40 | 84.5 | 55[1] |
| porous hollow fiber membrane | radiation-induced graft polymerization/gluteraldehyde | aminoacylase | 24 | 200 | 95[a] | 56[2] |
| nonwoven rayon/polyester blend | 1,1-carbonyldiimidazole | BSA | | 25 | | 58[3] |
| cotton terry cloth | tosyl chloride | β-galactosidase | 12 | 50 | 45 | 5[4] |
| cotton flannel cloth | PEI/dimethyl suberimidate | jack bean urease | 4 | 20 | 43 | 12[5] |
| cotton cloth | monolayer PEI/gluteraldehyde | invertase | 6 | 0.1% | 1670 U/g | 14[6] |
| cotton terry cloth | monolayer PEI/gluteraldehyde | β-galactosidase | 0.2 | 30 | 95.6 | this example |
| cotton terry cloth | multilayer PEI/gluteraldehyde | β-galactosidase | 0.2 | 250 | 92 | this example |
| nonwoven PET | multilayer PEI/gluteraldehyde | β-galactosidase | 0.2 | 250 | 87 | this example |
| nonwoven rayon (100%) | multilayer PEI/gluteraldehyde | β-galactosidase | 0.2 | 250 | 82 | this example |

[a]Protein yield
[1]Vol'f, L. A.; Shamolina, I. I.; Goncharova, N. A.; Lobova, A. B.; Gavrilova, V. P. Immobilization of enzymes on fibrous supports. Prikl. Biokhim. Mikrobiol. 1986, 22, 664–8.
[2]Kawai, T.; Nakamura, M.; Sugita, K.; Saito, K.; Sugo, T. High conversion in asymmetric hydrolysis during permeation through enzyme-multilayered porous hollow-fiber membranes. Biotechnol. Prog. 2001, 17, 872–875.
[3]Howlett, J. R.; Armstrong, D. W.; Yamazaki, H. Carbonyldiimidazole activation of a rayon/polyester cloth for covalent immobilization of proteins. Biotechnol. Tech. 1991, 5, 395–400.
[4]Albayrak, N.; Yang, S. T. Production of Galacto-oligosaccharides from lactose by *Aspergillus oryzae* β-galacosidase immobilized on cotton cloth. Biotechnol. Bioeng. 2002, 77, 8–19.
[5]Kamath, N.; Melo, J. S.; D'Souza, S. F. Urease immobilized on polyethyleneimine cotton cloth. Appl. Biochem. Biotechnol. 1988, 19, 251–8.
[6]Yamazaki, H.; Cheok, R. K. H.; Fraser, A. D. E. Immobilization of invertase on polyethylenimine-coated cotton cloth. Biotechnol. Lett. 1984, 6, 165–170.

TABLE 3

GOS Production by Various β-Galactosidases in Batch and Continuous Operations

| | | reaction conditions | | | | | |
|---|---|---|---|---|---|---|---|
| source of enzyme | mode of process[a] | Lactose concn. (g/L) | T (° C.) | pH | max GOS[b] (wt %) | productivity (g/L/h) | reference |
| B. circulans | batch (FE) | 45.6 | 40 | 6.0 | 24.0 | 2.2 | 59[7] |
| | continuous (IE, CSTR) | 45.6 | 40 | 6.0 | 40.0 | 4.2 | 24[8] |
| B. singularis | batch (IE) | 300 | 45 | 3.7 | 54.0[c] | 4.8 | 18[9] |
| | continuous (IE, PBR) | 100 | 45 | 4.8 | 55.0[c] | 4.4 | 18[9] |
| T. aquaticus | batch (IE) | 160 | 70 | 4.6 | 34.8 | 2.3 | 21[10] |
| K. lactis | batch (FE, UF) | 230 | 45 | 7.0 | 22.2 | 11.3 | 19[11] |
| | continuous (FE, UF) | 200 | 45 | 7.0 | 31.0 | 13.7 | 19[11] |
| A. oryzae | batch (FE) | 380 | 40 | 4.5 | 31.0 | 24.3 | 40[12] |
| | continuous (IE, FBR) | 200 | 40 | 4.5 | 21.7 | 80 | 5[13] |
| | | 400 | 40 | 4.5 | 26.6 | 106 | 5[13] |
| | | 400 | 40 | 4.5 | 26.6 | 6000 | this example |

[a]FE: free enzyme, IE: immobilized enzyme, CSTR: continuous stirred tank reactor, PBR: packed bed reactor, UF: ultrafiltration membrane reactor, FBR: fibrous bed (cotton cloth) reactor.
[b]Max GOS is a weight percent of GOS based on the total sugars in the reaction mixture.
[c]GOS content also includes disaccharides.
[7]Mozaffar, Z.; Nakanishi, K.; Matsuno, R.; Kamikuba, T. Production and properties of β-galactosidases from *Bacillus circulans*. Agric. Biol. Chem. 1984, 48, 3053–3061.
[8]Mozaffar, Z.; Nakanishi, K.; Matsuno, R. Continuous production of galacto-oligosaccharides from lactose using immobilized β-galactosidase from *Bacillus circulans*. Appl. Microbial. Biotechnol. 1986, 25, 224–228.
[9]Shin, H.-J.; Park, J.-M.; Yang, J.-W. Continuous production of galacto-oligosaccharides from lactose by *Bullera singularis* 250 Biotechnol. Prog., 2002, Vol. 18, No. 2 β-galactosidase immobilized in chitosan beads. Process Biochem. 1998, 33, 787–792.
[10]Berger, J. L.; Lee, B. H.; Lacroix, C. Oligosaccharides synthesis by free and immobilized β-galactosidases from *Thermus aquaticus* YT-1. Biotechnol. Lett. 1995, 17, 1077–1080.
[11]Foda, M. I.; Lopez-Leiva, M. H. Continuous production of oligosaccharides from whey using a membrane reactor. Process Biochem. 2000, 35, 581–587.
[12]Iwasaki, K.; Nakajima, M.; Nakao, S. Galacto-oligosaccharide production from lactose by an enzymatic batch reaction using β-galactosidase. Process Biochem. 1996, 31, 69–76.
[13]Albayrak, N.; Yang, S. T. Production of Galacto-oligosaccharides from lactose by *Aspergillus oryzae* β-galactosidase immobilized on cotton cloth. Biotechnol. Bioeng. 2002, 77, 8–19.

While the invention has been described by reference to certain preferred embodiments, it should be understood that numerous changes could be made within the spirit and scope of the inventive concepts described. Accordingly, it is intended that the invention not be limited to the disclosed embodiments, but that it have the full scope permitted by the language of the following claims.

We claim:

1. A multilayer enzyme immobilization process comprising:
    adsorbing a polyethyleneimine solution onto a fibrous matrix, said matrix including a plurality of fibrils;
    adding an enzyme in solution to said fibrous matrix comprises polyethyleneimine to enzyme ratio of between 1/33.3 to about 1/8.3;
    forming at least two layers of polyethyleneimine-enzyme aggregates on said fibrils; and
    cross-linking said polyethyleneimine-enzyme aggregates, wherein the polyethyleneimine-enzyme aggregates to matrix ratio is up to about 350 mg/g and having at least about a 5% immobilization yield.

2. The process of claim 1 wherein said enzyme is selected from β-galactosidase, lipase, lactate dehydrogenase, formate dehydrogenase, glucose isomerase, and combinations thereof.

3. The process of claim 2 wherein said β-galactosidase is isolated from a microorganism selected from *B. circulans, B. singularis, T. aquaticus, K. lactis, E. coli, A. oryzae, A. niger*, or combinations thereof.

4. The process of claim 3 wherein said β-galactosidase is isolated from the microorganism *A. oryzae, B. circulans, K. lactis*, or combinations thereof.

5. The process of claim 1 wherein said fibrous matrix is selected from cotton fibers, poly(ethylene terephthalate), glass fiber, wool, carbon fiber, ceramic fiber, paper, rayon, or combinations thereof.

6. The process of claim 1 wherein said fibrous matrix comprises an enzyme load that is less than about 350 mg/g fibrous matrix after adding said enzyme solution.

7. The process of claim 1 wherein said polyethyleneimine solution comprises polyethyleneimine solubilized in water.

8. The process of claim 7 wherein the concentration of polyethyleneimine in said polyethyleneimine solution is between about 0.001 mg/mL and the solubility of polyethyleneimine in water.

9. The process of claim 7 wherein the concentration of polyethyleneimine in said polyethyleneimine solution is between about 0.001 and about 30 mg/mL.

10. The process of claim 7 wherein the concentration of polyethyleneimine in said polyethyleneimine solution is about 2 mg/mL.

11. The process of claim 1 wherein said enzyme solution comprises enzyme solubilized in water.

12. The process of claim 11 wherein the concentration of enzyme in said enzyme solution is between about 0.001 and about 100 mg/mL.

13. The process of claim 1 wherein said polyethyleneimine molecules are positively charged, said enzyme is negatively charged, and said fibrous matrix comprises a balanced charge ratio of said polyethyleneimine to said enzyme.

14. The process of claim 1 wherein said fibrous matrix comprises a ratio of polyethyleneimine to enzyme of between about 1/33.3 and about 1/8.3 after adsorbing said polyethyleneimine solution in said fibrous matrix and adding said enzyme solution.

15. The process of claim 14 wherein said fibrous matrix comprises a polyethyleneimine to enzyme ratio of between about 1/20 and about 1/25 after adsorbing said polyethyleneimine solution in said fibrous matrix and adding said enzyme solution.

16. The process of claim 15 wherein said fibrous matrix comprises a polyethyleneimine to enzyme ratio of between about 1/22 and about 1/25.

17. The process of claim 1 further comprising maintaining said polyethyleneimine and enzme solution at a pH in the range of between about 4 and about 10 during said forming at least two layers of polyethyleneimine-enzyme aggregates.

18. The process of claim 17 wherein said pH is between about 6 and about 8.

19. The process of claim 1 further comprising maintaining said enzyme solution at a temperature that is less than about 65° C. prior to adding to said fibrous matrix.

20. The process of claim 19 further comprising maintaining said enzyme solution at a temperature that is between about 0 and about 25° C. prior to adding to said fibrous matrix.

21. The process of claim 1 further comprising forming at least two layers of polyethyleneimine-enzyme aggregates on said fibrils at a temperature that is less than about 65° C.

22. The process of claim 1 further comprising forming at least two layers of polyethyleneimine-enzyme aggregates on said fibrils at a temperature that is between about 0° C. and room temperature.

23. The process of claim 1 further comprising forming at least two layers of polyethyleneimine-enzyme aggregates on said fibrils such that said aggregates completely cover said fibrils.

24. The process of claim 1 wherein said cross-linking of said polyethyleneimine-enzyme aggregates is performed by applying an enzyme fixative.

25. The process of claim 24 wherein said enzyme fixative is an aldehyde or keto compound that can form covalent bonds with the amine groups of an enzyme protein.

26. The process of claim 24 wherein said enzyme fixative is gluteraldehyde, formaldehyde, or combinations thereof.

27. The process of claim 26 wherein said gluteraldehyde comprises a solution of gluteraldehyde and water.

28. The process of claim 27 wherein said gluteraldehyde solution has a concentration between about 0.05 and about 0.2%.

29. The process of claim 28 wherein said gluteraldehyde solution has a concentration of about 0.1%.

30. The process of claim 24 wherein said enzyme fixative has a pH between about 6 and about 8.

31. The process of claim 24 wherein said enzyme fixative is reacted with said polyethyleneimine-enzyme aggregates for a time sufficient to cross-link said polyethyleneimine-enzyme aggregates.

32. The process of claim 31 wherein said enzyme fixative is reacted with said polyethyleneimine-enzyme aggregates for at least about 5 minutes.

33. The process of claim 24 further comprising maintaining said enzyme fixative at a temperature that is less than about 65° C. prior to cross-linking said polyethyleneimine-enzyme aggregates.

34. The process of claim 1 further comprising washing said fibrils and said cross-linked polyethyleneimine-enzyme aggregates formed thereon with distilled water and acidic buffer subsequent to said cross-linking.

35. The process of claim 1 wherein said process produces an immobilized enzyme yield that is less than or equal to about 100%.

36. The process of claim 1 wherein said process produces an immobilized enzyme yield that is at least about 5%.

* * * * *